United States Patent
Kavazov et al.

(10) Patent No.: US 8,172,929 B2
(45) Date of Patent: May 8, 2012

(54) SYSTEMS AND METHODS ALLOWING FOR RESERVOIR AIR BUBBLE MANAGEMENT

(75) Inventors: Julian D. Kavazov, Arcadia, CA (US); Rafael Bikovsky, Oak Park, CA (US); Arsen Ibranyan, Glendale, CA (US); David Hezzell, Thousand Oaks, CA (US); Christopher G. Griffin, Sylmar, CA (US); Mike Lee, Glendale, CA (US); Truong Gia Luan, Winnetka, CA (US); Benjamin X. Shen, Davis, CA (US); Thomas Miller, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 13/118,358

(22) Filed: May 27, 2011

(65) Prior Publication Data

US 2011/0230834 A1   Sep. 22, 2011

Related U.S. Application Data

(62) Division of application No. 12/111,815, filed on Apr. 29, 2008, now Pat. No. 7,959,715.

(60) Provisional application No. 60/927,032, filed on Apr. 30, 2007.

(51) Int. Cl.
*B01D 53/22* (2006.01)
*B01D 19/00* (2006.01)
*A61M 5/14* (2006.01)
*A61M 5/142* (2006.01)

(52) U.S. Cl. ............... 96/6; 95/45; 604/140; 604/187; 604/190; 604/191; 604/244; 600/578; 222/394; 222/399; 222/401; 29/890.09

(58) Field of Classification Search ............ 96/6; 95/45; 604/140, 146, 187, 190, 191, 244; 600/578; 222/394, 399, 401; 29/890.09
See application file for complete search history.

(56) References Cited

U.S. PATENT DOCUMENTS
1,948,982 A   2/1934  Cutter
(Continued)

FOREIGN PATENT DOCUMENTS
DE  1020040 55 870 A1   5/2006
(Continued)

OTHER PUBLICATIONS

International Search Report and Written Opinion for PCT application No. PCT/US2008/082193 dated Jun. 29, 2010.
(Continued)

*Primary Examiner* — Jason M Greene
(74) *Attorney, Agent, or Firm* — Foley & Lardner LLP

(57) ABSTRACT

Various embodiments of the present invention are directed to limiting a presence of air bubbles in fluidic media in a reservoir. Air passages may allow air to escape from fluidic media in a reservoir. Membranes may allow for trapping air bubbles in fluidic media before fluidic media enters a reservoir. A membrane may allow air to flow from a first reservoir containing fluidic media to a second reservoir while plunger heads within each of the reservoirs are moved within the reservoirs. An inner reservoir with a membrane may be moveable within an outer reservoir to allow air to move from the outer reservoir to the inner reservoir. An inner reservoir containing pressurized gas may allow fluidic media to be transferred to an outer reservoir.

15 Claims, 18 Drawing Sheets

U.S. PATENT DOCUMENTS

| | | |
|---|---|---|
| 2,064,815 A | 12/1936 | Armstrong |
| 2,570,625 A | 10/1951 | Zimmerman et al. |
| 2,644,450 A | 7/1953 | Krewson |
| 2,973,758 A | 3/1961 | Murrish |
| 3,085,454 A * | 4/1963 | Federighi .................... 604/140 |
| 3,342,180 A | 9/1967 | Ellsworth et al. |
| 3,623,474 A | 11/1971 | Heilman et al. |
| 3,662,753 A | 5/1972 | Tassell |
| 3,802,430 A | 4/1974 | Schwebel et al. |
| 3,923,058 A * | 12/1975 | Weingarten .................... 604/191 |
| 3,963,151 A | 6/1976 | North, Jr. |
| 4,064,879 A | 12/1977 | Leibinsohn |
| 4,089,624 A | 5/1978 | Nichols et al. |
| 4,093,108 A * | 6/1978 | Hein et al. .................... 222/401 |
| 4,117,841 A | 10/1978 | Perrotta et al. |
| 4,215,701 A | 8/1980 | Raitto |
| 4,219,055 A | 8/1980 | Wright |
| 4,373,535 A | 2/1983 | Martell |
| 4,392,850 A | 7/1983 | Elias et al. |
| 4,434,820 A | 3/1984 | Glass |
| 4,448,206 A | 5/1984 | Martell |
| 4,493,704 A | 1/1985 | Beard et al. |
| 4,568,336 A | 2/1986 | Cooper |
| 4,572,210 A | 2/1986 | McKinnon |
| 4,585,435 A | 4/1986 | Vaillancourt |
| 4,684,365 A | 8/1987 | Reinicke |
| 4,684,366 A | 8/1987 | Denny et al. |
| 4,703,763 A | 11/1987 | McAlister et al. |
| 4,743,249 A | 5/1988 | Loveland |
| 4,744,955 A | 5/1988 | Shapiro |
| 4,759,756 A | 7/1988 | Forman et al. |
| 4,838,857 A | 6/1989 | Strowe et al. |
| 4,865,592 A | 9/1989 | Rycroft |
| 4,883,101 A | 11/1989 | Strong |
| 4,913,703 A | 4/1990 | Pasqualucci et al. |
| 4,957,637 A | 9/1990 | Cornell |
| 4,976,696 A | 12/1990 | Sanderson et al. |
| 4,986,820 A | 1/1991 | Fischer |
| 5,002,527 A | 3/1991 | Reller et al. |
| 5,049,129 A | 9/1991 | Zdeb et al. |
| 5,053,001 A | 10/1991 | Reller et al. |
| 5,062,834 A | 11/1991 | Gross et al. |
| 5,090,963 A | 2/1992 | Gross et al. |
| 5,156,591 A | 10/1992 | Gross et al. |
| 5,176,502 A | 1/1993 | Sanderson et al. |
| 5,186,805 A | 2/1993 | Gross et al. |
| 5,190,522 A | 3/1993 | Wojcicki et al. |
| 5,203,506 A | 4/1993 | Gross et al. |
| 5,232,449 A | 8/1993 | Stern et al. |
| 5,242,406 A | 9/1993 | Gross et al. |
| 5,242,408 A | 9/1993 | Jhuboo et al. |
| 5,246,147 A | 9/1993 | Gross |
| 5,254,096 A | 10/1993 | Rondelet et al. |
| 5,259,732 A | 11/1993 | Stern |
| 5,261,884 A | 11/1993 | Stern et al. |
| 5,275,582 A | 1/1994 | Wimmer |
| 5,284,570 A | 2/1994 | Savage et al. |
| 5,292,318 A | 3/1994 | Haber et al. |
| 5,295,966 A | 3/1994 | Stern et al. |
| 5,295,967 A | 3/1994 | Rondelet et al. |
| 5,312,364 A | 5/1994 | Jacobs |
| 5,356,632 A | 10/1994 | Gross et al. |
| 5,367,891 A | 11/1994 | Furuyama |
| 5,385,559 A | 1/1995 | Mannix |
| 5,387,450 A | 2/1995 | Stewart |
| 5,407,434 A | 4/1995 | Gross |
| 5,409,236 A | 4/1995 | Therrien |
| 5,415,648 A * | 5/1995 | Malay et al. .................... 604/181 |
| 5,425,706 A | 6/1995 | Gross et al. |
| 5,496,285 A | 3/1996 | Schumacher et al. |
| 5,527,288 A | 6/1996 | Gross et al. |
| 5,533,964 A | 7/1996 | Halperin et al. |
| 5,697,916 A | 12/1997 | Schraga |
| 5,704,520 A | 1/1998 | Gross |
| 5,800,420 A | 9/1998 | Gross et al. |
| 5,807,375 A | 9/1998 | Gross et al. |
| 5,820,622 A | 10/1998 | Gross et al. |
| 5,848,991 A | 12/1998 | Gross et al. |
| 5,851,549 A | 12/1998 | Svec |
| 5,858,001 A | 1/1999 | Tsals et al. |
| 5,865,803 A | 2/1999 | Major |
| 5,871,125 A | 2/1999 | Gross |
| 5,933,287 A | 8/1999 | Muller |
| 5,951,523 A | 9/1999 | Osterlind et al. |
| 5,954,697 A | 9/1999 | Srisathapat et al. |
| 5,957,889 A | 9/1999 | Poulsen et al. |
| 5,984,894 A | 11/1999 | Poulsen et al. |
| 5,997,501 A | 12/1999 | Gross et al. |
| 6,003,736 A | 12/1999 | Ljunggren |
| 6,033,377 A | 3/2000 | Rasmussen et al. |
| 6,077,252 A * | 6/2000 | Siegel .................... 604/191 |
| 6,088,608 A | 7/2000 | Schulman et al. |
| 6,099,504 A | 8/2000 | Gross et al. |
| 6,119,028 A | 9/2000 | Schulman et al. |
| 6,126,643 A | 10/2000 | Vaillancouert |
| 6,186,982 B1 | 2/2001 | Gross et al. |
| 6,229,584 B1 | 5/2001 | Chuo et al. |
| 6,242,665 B1 | 6/2001 | Malowaniec |
| 6,248,093 B1 | 6/2001 | Moberg |
| 6,261,272 B1 | 7/2001 | Gross et al. |
| 6,275,717 B1 | 8/2001 | Gross et al. |
| 6,277,095 B1 | 8/2001 | Kriesel et al. |
| 6,312,409 B1 | 11/2001 | Gross |
| 6,314,317 B1 | 11/2001 | Willis |
| 6,346,095 B1 | 2/2002 | Gross et al. |
| 6,364,865 B1 | 4/2002 | Lavi et al. |
| 6,406,455 B1 | 6/2002 | Willis et al. |
| 6,423,035 B1 | 7/2002 | Das et al. |
| 6,440,096 B1 | 8/2002 | Lastovich et al. |
| 6,450,993 B1 | 9/2002 | Lin |
| 6,461,329 B1 | 10/2002 | Van Antwerp et al. |
| 6,474,219 B2 | 11/2002 | Klitmose et al. |
| 6,478,771 B1 | 11/2002 | Lavi et al. |
| 6,485,461 B1 | 11/2002 | Mason et al. |
| 6,485,465 B2 | 11/2002 | Moberg et al. |
| 6,490,483 B2 | 12/2002 | Willis |
| 6,503,225 B1 | 1/2003 | Kirsch et al. |
| 6,508,788 B2 | 1/2003 | Preuthun |
| 6,537,251 B2 | 3/2003 | Klitmose |
| 6,551,285 B1 | 4/2003 | Bierman |
| 6,572,600 B1 | 6/2003 | Roe et al. |
| 6,585,707 B2 | 7/2003 | Cabiri et al. |
| 6,589,229 B1 | 7/2003 | Connelly et al. |
| 6,595,956 B1 | 7/2003 | Gross et al. |
| 6,607,509 B2 | 8/2003 | Bobroff et al. |
| 6,607,513 B1 | 8/2003 | Down et al. |
| 6,613,019 B2 | 9/2003 | Munk |
| 6,616,627 B2 | 9/2003 | Willis et al. |
| 6,626,874 B1 | 9/2003 | Duchamp |
| 6,641,565 B1 | 11/2003 | Lavi et al. |
| 6,641,566 B2 | 11/2003 | Douglas et al. |
| 6,645,181 B1 | 11/2003 | Lavi et al. |
| 6,656,147 B1 | 12/2003 | Gertsek et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,689,100 B2 | 2/2004 | Connelly et al. |
| 6,692,457 B2 | 2/2004 | Flaherty |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,195 B2 | 4/2004 | Nolan et al. |
| 6,719,734 B1 | 4/2004 | Harkless |
| 6,723,068 B2 | 4/2004 | Lavi et al. |
| 6,723,072 B2 | 4/2004 | Flaherty et al. |
| 6,723,074 B1 * | 4/2004 | Halseth .................... 604/191 |
| 6,740,059 B2 | 5/2004 | Flaherty |
| 6,740,072 B2 | 5/2004 | Starkweather et al. |
| 6,749,587 B2 | 6/2004 | Flaherty |
| 6,767,188 B2 | 7/2004 | Vrane et al. |
| 6,768,425 B2 | 7/2004 | Flaherty et al. |
| 6,786,246 B2 | 9/2004 | Ohms et al. |
| 6,796,965 B2 | 9/2004 | Dumaresq-Lucas et al. |
| 6,808,506 B2 | 10/2004 | Lastovich et al. |
| 6,827,702 B2 | 12/2004 | Lebel et al. |
| 6,830,558 B2 | 12/2004 | Flaherty et al. |
| 6,830,560 B1 | 12/2004 | Gross et al. |

| | | |
|---|---|---|
| 6,886,724 B2 | 5/2005 | Hung |
| 6,899,699 B2 | 5/2005 | Enggaard |
| 6,915,147 B2 | 7/2005 | Lebel et al. |
| 6,936,006 B2 | 8/2005 | Sabra |
| 6,939,324 B2 | 9/2005 | Gonnelli et al. |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 7,220,245 B2 | 5/2007 | Kriesel |
| 7,220,889 B2 | 5/2007 | Sigurjonsson et al. |
| 7,318,816 B2 | 1/2008 | Bobroff et al. |
| 7,323,142 B2 | 1/2008 | Pendo et al. |
| 7,390,294 B2 | 6/2008 | Hassler, Jr. |
| 7,399,484 B2 | 7/2008 | Ellefson et al. |
| 7,686,787 B2 | 3/2010 | Moberg et al. |
| 7,828,765 B2 * | 11/2010 | Hallahan et al. ................ 604/91 |
| 7,858,112 B2 | 12/2010 | Hatanaka et al. |
| 2001/0041869 A1 | 11/2001 | Causey et al. |
| 2002/0040208 A1 | 4/2002 | Flaherty et al. |
| 2002/0072733 A1 | 6/2002 | Flaherty |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0104032 A1 | 6/2003 | Sawhney et al. |
| 2003/0125672 A1 | 7/2003 | Adair et al. |
| 2003/0167035 A1 | 9/2003 | Flaherty et al. |
| 2003/0167036 A1 | 9/2003 | Flaherty |
| 2003/0199824 A1 | 10/2003 | Mahoney et al. |
| 2003/0199825 A1 | 10/2003 | Flaherty |
| 2003/0212364 A1 | 11/2003 | Mann et al. |
| 2003/0229310 A1 | 12/2003 | Flaherty et al. |
| 2003/0233069 A1 | 12/2003 | Gillespie et al. |
| 2004/0002682 A1 | 1/2004 | Kovelman et al. |
| 2004/0010207 A1 | 1/2004 | Flaherty et al. |
| 2004/0011866 A1 | 1/2004 | Saad |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0073095 A1 | 4/2004 | Causey et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116866 A1 | 6/2004 | Gorman et al. |
| 2004/0158207 A1 | 8/2004 | Hunn et al. |
| 2004/0199140 A1 | 10/2004 | Rue et al. |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0236201 A1 | 11/2004 | Lebel et al. |
| 2004/0260233 A1 | 12/2004 | Garibotto et al. |
| 2005/0022274 A1 | 1/2005 | Campbell et al. |
| 2005/0065760 A1 | 3/2005 | Murtfeldt et al. |
| 2005/0101920 A1 | 5/2005 | Keane et al. |
| 2005/0119618 A1 | 6/2005 | Gonnelli |
| 2005/0137530 A1 | 6/2005 | Campbell et al. |
| 2006/0184119 A1 | 8/2006 | Remde et al. |
| 2006/0253085 A1 | 11/2006 | Geismar et al. |
| 2006/0264835 A1 | 11/2006 | Nielsen et al. |
| 2006/0264894 A1 | 11/2006 | Moberg et al. |
| 2007/0062068 A1 | 3/2007 | Li |
| 2007/0066939 A1 | 3/2007 | Krulevich et al. |
| 2007/0073235 A1 | 3/2007 | Estes et al. |
| 2007/0293826 A1 | 12/2007 | Wall et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0077081 A1 | 3/2008 | Mounce et al. |
| 2008/0097291 A1 | 4/2008 | Hanson et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0255521 A1 * | 10/2008 | Kubo et al. .................. 604/191 |
| 2008/0269682 A1 | 10/2008 | Kavazov et al. |
| 2009/0326475 A1 * | 12/2009 | Carlyon ........................ 604/191 |

FOREIGN PATENT DOCUMENTS

| | | |
|---|---|---|
| DE | 202007006363 U1 | 8/2007 |
| EP | 1 462 134 A1 | 9/2004 |
| EP | 1 527 792 A1 | 5/2005 |
| EP | 1 347 705 | 12/2005 |
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| FR | 1496026 | 9/1967 |
| GB | 1 452 104 | 10/1976 |
| GB | 2 176 711 | 1/1987 |
| GB | 2 207 652 | 2/1989 |
| WO | WO-95/23015 | 11/1995 |
| WO | WO-96/26702 | 9/1996 |
| WO | WO-97/44078 | 11/1997 |
| WO | WO-97/46203 | 12/1997 |
| WO | WO-99/48546 | 9/1999 |
| WO | WO-99/59665 | 11/1999 |
| WO | WO-00/47254 A1 | 8/2000 |
| WO | WO-00/69488 | 11/2000 |
| WO | WO-01/70307 A1 | 9/2001 |
| WO | WO-01/76684 A1 | 10/2001 |
| WO | WO-02/02165 A2 | 1/2002 |
| WO | WO-02/20073 A2 | 3/2002 |
| WO | WO-02/28454 A2 | 4/2002 |
| WO | WO-02/40083 A2 | 5/2002 |
| WO | WO-02/49509 A2 | 6/2002 |
| WO | WO-02/068015 A2 | 9/2002 |
| WO | WO-03/006090 A1 | 1/2003 |
| WO | WO-03/024504 A2 | 3/2003 |
| WO | WO-03/026728 A1 | 4/2003 |
| WO | WO-03/033051 A1 | 4/2003 |
| WO | WO-03/059372 A3 | 7/2003 |
| WO | WO-03/072172 A2 | 9/2003 |
| WO | WO-03/074121 A1 | 9/2003 |
| WO | WO-03/090509 A2 | 11/2003 |
| WO | WO-03/090819 A2 | 11/2003 |
| WO | WO-03/090838 A1 | 11/2003 |
| WO | WO-03/103758 A1 | 12/2003 |
| WO | WO-03/103763 A1 | 12/2003 |
| WO | WO-2004/006981 A2 | 1/2004 |
| WO | WO-2004/006982 A2 | 1/2004 |
| WO | WO-2004/030716 A2 | 4/2004 |

| | | | |
|---|---|---|---|
| WO | WO-2004/030717 A2 | 4/2004 |
| WO | WO-2004/047641 A2 | 6/2004 |
| WO | WO-2004/060436 A2 | 7/2004 |
| WO | WO-2004/093648 A2 | 11/2004 |
| WO | WO-2004/098390 A2 | 11/2004 |
| WO | WO-2004/098454 A2 | 11/2004 |
| WO | WO-2004/098683 A1 | 11/2004 |
| WO | WO-2004/110526 A1 | 12/2004 |
| WO | WO-2005/000382 A2 | 1/2005 |
| WO | WO-2005/072795 A2 | 8/2005 |
| WO | WO-2005/094920 A1 | 10/2005 |
| WO | WO-2005/097237 A1 | 10/2005 |
| WO | WO-2006/015922 A1 | 2/2006 |
| WO | WO-2006/018425 A3 | 2/2006 |
| WO | WO-2006/018447 A3 | 2/2006 |
| WO | WO-2006/024671 A1 | 3/2006 |
| WO | WO-2006/024672 A1 | 3/2006 |
| WO | WO-2006/032692 A1 | 3/2006 |
| WO | WO-2006/042811 A3 | 4/2006 |
| WO | WO-2006/058435 A2 | 6/2006 |
| WO | WO-2006/072416 A2 | 7/2006 |
| WO | WO-2006/075016 A1 | 7/2006 |
| WO | WO-2006/077262 A1 | 7/2006 |
| WO | WO-2006/077263 A1 | 7/2006 |
| WO | WO-2006/084464 A1 | 8/2006 |
| WO | WO-2006/086980 A1 | 8/2006 |
| WO | WO-2006/089547 A1 | 8/2006 |
| WO | WO-2006/089548 A1 | 8/2006 |
| WO | WO-2006/089965 A1 | 8/2006 |
| WO | WO-2006/096746 A1 | 9/2006 |
| WO | WO-2006/097453 A1 | 9/2006 |
| WO | WO 2006/104806 A2 | 10/2006 |
| WO | WO-2006/108775 A2 | 10/2006 |
| WO | WO-2006/108809 A1 | 10/2006 |
| WO | WO-2006/116997 A1 | 11/2006 |
| WO | WO-2006/120253 A2 | 11/2006 |
| WO | WO-2006/125692 A1 | 11/2006 |
| WO | WO-2007/000425 A2 | 1/2007 |
| WO | WO-2007/000426 A2 | 1/2007 |
| WO | WO-2007/000427 A1 | 1/2007 |
| WO | WO-2007/038091 A2 | 4/2007 |
| WO | WO-2007/062068 A2 | 5/2007 |
| WO | WO-2007/071255 A1 | 6/2007 |
| WO | WO 2007/076641 A1 | 7/2007 |
| WO | WO-2007/087808 A1 | 8/2007 |
| WO | WO-2007/130809 A2 | 11/2007 |
| WO | WO-2008/024614 A2 | 2/2008 |
| WO | WO-2008/093063 A2 | 8/2008 |
| WO | WO-2008/151241 A2 | 12/2008 |

OTHER PUBLICATIONS

International Search Report and Written Opinion for related PCT Application No. PCT/US2007/076641 dated Feb. 27, 2008.
International Search Report dated May 15, 2008 for related PCT Application No. PCT/US2007/076679.
Office Action dated Apr. 30, 2009 from related U.S. Appl. No. 12/027,963.
Office Action dated Aug. 4, 2009 from related U.S. Appl. No. 12/411,247.
Office Action dated Dec. 22, 2010 from related U.S. Appl. No. 12/111,815.
Office Action dated Dec. 30, 2010 from related U.S. Appl. No. 12/107,580.
Office Action dated Dec. 9, 2010 from related U.S. Appl. No. 12/099,738.
Office Action dated Jan. 14, 2010 from related U.S. Appl. No. 12/411,247.
Office Action dated Jan. 7, 2010 from related U.S. Appl. No. 11/964,649.
Office Action dated Jul. 10, 2009 from related U.S. Appl. No. 12/411,236.
Office Action dated Jul. 21, 2010 from related U.S. Appl. No. 12/099,738.
Office Action dated Jul. 8, 2009 from related U.S. Appl. No. 11/964,649.
Office Action dated Jun. 16, 2010 from related U.S. Appl. No. 12/027,963.
Office Action dated Mar. 4, 2010 from related U.S. Appl. No. 12/099,738.
Office Action dated Nov. 10, 2009 from related U.S. Appl. No. 12/099,738.
Office Action dated Oct. 23, 2009 from related U.S. Appl. No. 12/411,236.
Office Action dated Sep. 24, 2009 from related U.S. Appl. No. 12/027,963.
Partial PCT Search Report dated Feb. 9, 2009 for related PCT application No. PCT/US2008/082186.
Partial PCT Search Report dated Mar. 5, 2009 from related PCT application No. PCT/US2008/082187.
Search Report dated Apr. 28, 2009 from related PCT application No. PCT/US2008/082186.
Search Report dated Feb. 3, 2009 from related PCT application No. PCT/US2008/082185.
U.S. Office Action dated Mar. 8, 2011 from related U.S. Appl. No. 12/411,247.
US Notice of Allowance dated Mar. 3, 2011 from related U.S. Appl. No. 12/107,580.
US Office Action dated Aug. 18, 2010 from related U.S. Appl. No. 12/107,580.
US Office Action dated Feb. 23, 2011 from related U.S. Appl. No. 12/411,236.
US Office Action dated Mar. 29, 2011 from related U.S. Appl. No. 11/964,649.
US Office Action dated Oct. 1, 2010 U.S. Appl. No. 12/411,247.
US Office Action dated Oct. 15, 2010 from related U.S. Appl. No. 12/027,963.
US Office Action dated Sep. 28, 2010 from related U.S. Appl. No. 12/411,236.
International Search Report dated Jun. 5, 2009 from PCT Application No. PCT/US2008/082187.
PCT Search Report dated May 15, 2008 for PCT application No. PCT/US2007/076679.
US Notice of Allowance dated Jul. 27, 2011 from related U.S. Appl. No. 12/411,247.

* cited by examiner

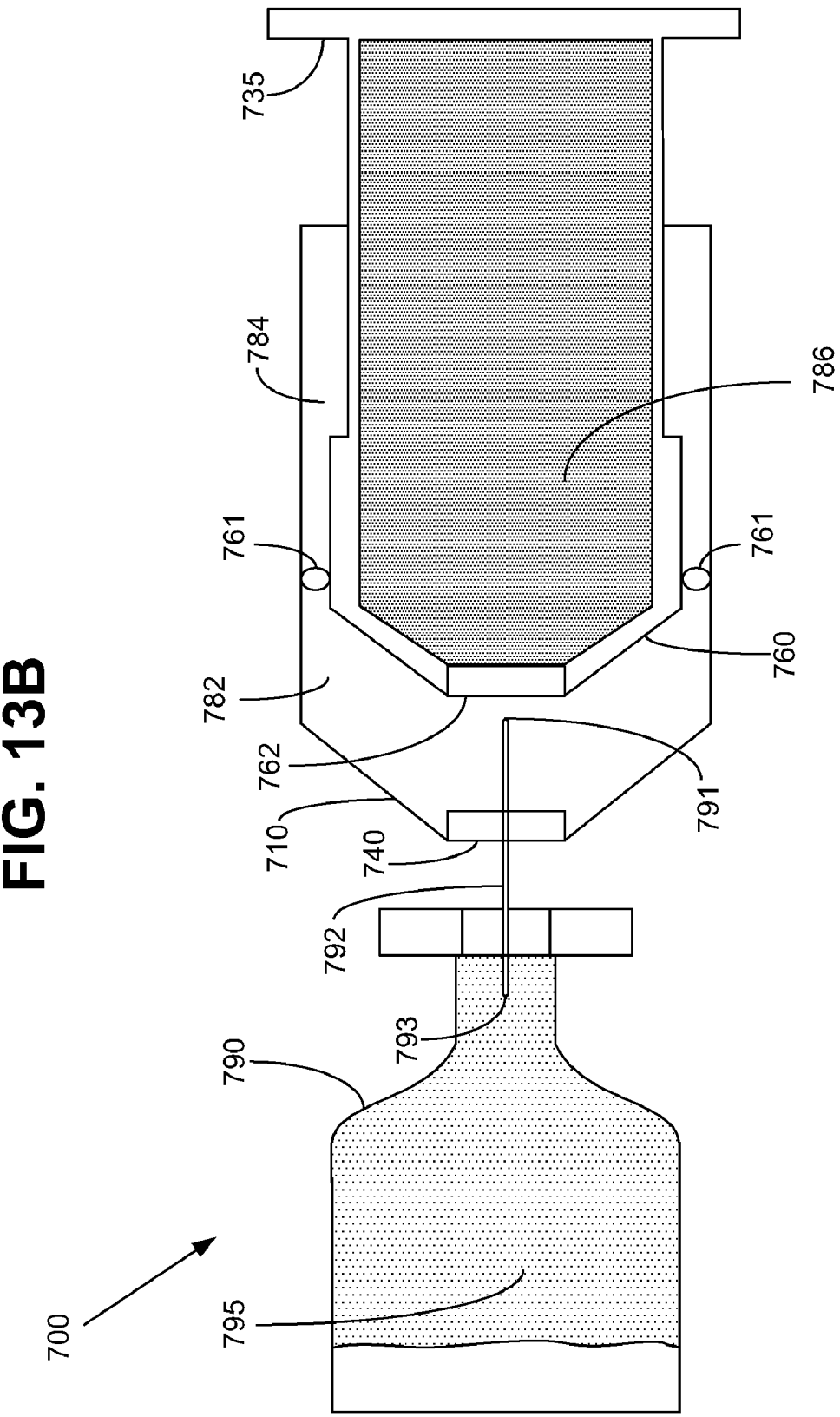

SYSTEMS AND METHODS ALLOWING FOR RESERVOIR AIR BUBBLE MANAGEMENT

CROSS-REFERENCE TO RELATED PATENT APPLICATIONS

The present application is a divisional application of U.S. Ser. No. 12/111,815, filed Apr. 29, 2008, now allowed, entitled "Systems and Methods Allowing for Reservoir Air Bubble Management", which claims priority to U.S. Provisional Application Ser. No. 60/927,032, filed Apr. 30, 2007, entitled "Inserting, Reservoir Filling, Bubble Management, Fluid Flow Connections and Infusion Medium Delivery Systems and Methods with Same", the entire contents of both of which are incorporated by reference herein.

Embodiments of the present invention relate to PCT International Application No. PCT/US2007/076641, filed Aug. 23, 2007, the contents of which are incorporated by reference herein, and which claims the benefit of U.S. Provisional Application Ser. No. 60/927,032, filed Apr. 30, 2007.

BACKGROUND OF THE INVENTION

1. Field of the Invention

Embodiments of the present invention relate generally to systems and methods with reservoirs and, in specific embodiments, to systems and methods allowing for reservoir air bubble management.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have also been configured in implantable devices, which are implanted inside of the body of a patient. External pump type delivery devices include devices designed for use in a stationary location, such as a hospital, a clinic, or the like, and further include devices configured for ambulatory or portable use, such as devices that are designed to be carried by a patient, or the like. External pump type delivery devices may be connected in fluid flow communication to a patient or user, for example, through a suitable hollow tubing. The hollow tubing may be connected to a hollow needle that is designed to pierce the skin of the patient and to deliver a fluidic medium therethrough. Alternatively, the hollow tubing may be connected directly to the patient as through a cannula, or the like.

Examples of some external pump type delivery devices are described in the following references: (i) Published PCT Application WO 01/70307 (PCT/US01/09139), entitled "Exchangeable Electronic Cards for Infusion Devices"; (ii) Published PCT Application WO 04/030716 (PCT/US2003/028769), entitled "Components and Methods for Patient Infusion Device"; (iii) Published PCT Application WO 04/030717 (PCT/US2003/029019), entitled "Dispenser Components and Methods for Infusion Device"; (iv) U.S. Patent Application Pub. No. 2005/0065760, entitled "Method for Advising Patients Concerning Doses Of Insulin"; and (v) U.S. Pat. No. 6,589,229, entitled "Wearable Self-Contained Drug Infusion Device", each of which is incorporated by reference herein in its entirety.

As compared to syringes and insulin pens, pump type delivery devices can be significantly more convenient to a patient, in that doses of insulin may be calculated and delivered automatically to a patient at any time during the day or night. Furthermore, when used in conjunction with glucose sensors or monitors, insulin pumps may be automatically controlled to provide appropriate doses of a fluidic medium at appropriate times of need, based on sensed or monitored levels of blood glucose. As a result, pump type delivery devices have become an important aspect of modern medical treatments of various types of medical conditions, such as diabetes, and the like. As pump technologies improve and doctors and patients become more familiar with such devices, external medical infusion pump treatments are expected to increase in popularity and are expected to increase substantially in number over the next decade.

SUMMARY OF THE DISCLOSURE

Various embodiments of the present invention are directed to limiting a presence of air bubbles in fluidic media in a reservoir. Air passages may allow air to escape from fluidic media in a reservoir. Membranes may allow for trapping air bubbles in fluidic media before fluidic media enters a reservoir. A membrane may allow air to flow from a first reservoir containing fluidic media to a second reservoir while plunger heads within each of the reservoirs are moved within the reservoirs. An inner reservoir with a membrane may be moveable within an outer reservoir to allow air to move from the outer reservoir to the inner reservoir. An inner reservoir containing pressurized gas may allow fluidic media to be transferred to an outer reservoir.

A system for managing air bubbles in accordance with an embodiment of the present invention may include, but is not limited to, a reservoir and one or more filters. The reservoir may have an interior volume for containing fluidic media. The reservoir may have a port for expelling fluidic media from the interior volume of the reservoir. The reservoir may have one or more air passages that extend from the interior volume of the reservoir to an outer surface of the reservoir. Each of the one or more filters may be located in a respective air passage of the one or more air passages.

In various embodiments, each of the one or more filters may be located at an end of the respective air passage of the one or more air passages. In some embodiments, each of the one or more filters may comprise a hydrophobic material. Each of the one or more filters may be positioned at the end of the respective air passage of the one or more air passages so as to substantially prevent fluidic media from entering the respective air passage of the one or more air passages in a case where fluidic media is in the interior volume of the reservoir.

In various embodiments, the reservoir may have a fluid channel that leads from the interior volume of the reservoir to the port of the reservoir. The one or more air passages may surround the fluid channel of the reservoir. Additionally, in various embodiments, each of the one or more filters may be configured to allow air in the interior volume of the reservoir to pass through the filter and to exit the reservoir through the respective air passage of the one or more air passages. In some embodiments, each of the one or more air passages may exit the reservoir on a same side of the reservoir where the port of the reservoir is located. In some embodiments, each of the one or more air passages may allow air to exit the reservoir on a same side of the reservoir where fluidic media is expelled from the reservoir.

A method of making a system for managing air bubbles in accordance with an embodiment of the present invention may include, but is not limited to, (i) providing a reservoir having an interior volume for containing fluidic media, the reservoir having a port for expelling fluidic media from the interior volume of the reservoir, the reservoir having one or more air passages that extend from the interior volume of the reservoir to an outer surface of the reservoir and (ii) locating each of one or more filters in a respective air passage of the one or more air passages.

In an embodiment for a system for managing air bubbles, the system may include, but is not limited to, a reservoir, a plunger head, and a membrane. The plunger head may be moveable within the reservoir. The reservoir may have an interior volume for containing fluidic media on one side of the plunger head. The reservoir may have a chamber on an opposite side of the plunger head from the interior volume of the reservoir. The reservoir may have a channel connecting the interior volume of the reservoir with the chamber of the reservoir. The membrane may be for allowing air to pass from the interior volume of the reservoir to the chamber of the reservoir through the channel of the reservoir and for inhibiting fluidic media from passing from the interior volume of the reservoir to the chamber of the reservoir through the channel of the reservoir.

In various embodiments, the system may include a bias member connected between a surface of the reservoir and the plunger head within the chamber of the reservoir. In some embodiments, the bias member may comprise a spring.

In various embodiments, the system may include a valve for allowing a vacuum to be applied to the chamber of the reservoir. In various embodiments, the membrane may comprise a hydrophobic material.

A method of making a system for managing air bubbles in accordance with an embodiment of the present invention may include, but is not limited to, (i) providing a reservoir, (ii) locating a plunger head moveable within the reservoir, the reservoir having a interior volume for containing fluidic media on one side of the plunger head, the reservoir having a chamber on an opposite side of the plunger head from the interior volume of the reservoir, the reservoir having a channel connecting the interior volume of the reservoir with the chamber of the reservoir, and (iii) providing a membrane for allowing air to pass from the interior volume of the reservoir to the chamber of the reservoir through the channel of the reservoir and for inhibiting fluidic media from passing from the interior volume of the reservoir to the chamber of the reservoir through the channel of the reservoir.

In an embodiment for a system for managing air bubbles, the system may include, but is not limited to, a reservoir, a plunger head, a bellows member, and a membrane. The reservoir may have an interior volume for containing fluidic media. The plunger head may be moveable within the reservoir. The plunger head may have a channel from a first surface of the plunger head to a second surface of the plunger head. The first surface of the plunger head may be contact with fluidic media in a case where fluidic media is in the interior volume of the reservoir. The bellows member may be connected to the plunger head. The membrane may be located within the channel of the plunger head. The membrane may be configured to allow air to pass from the interior volume of the reservoir to an interior volume of the bellows member through the channel of the plunger head. The membrane may be configured to inhibit fluidic media from passing from the interior volume of the reservoir to the interior volume of the bellows member through the channel of the plunger head in a case where fluidic media is in the interior volume of the reservoir.

A method of making a system for managing air bubbles in accordance with an embodiment of the present invention may include, but is not limited to, (i) providing a reservoir having an interior volume for containing fluidic media, (ii) locating a plunger head moveable within the reservoir, the plunger head having a channel from a first surface of the plunger head to a second surface of the plunger head, the first surface of the plunger head in contact with fluidic media in a case where fluidic media is in the interior volume of the reservoir, (iii) providing a bellows member connected to the plunger head, and (iv) locating a membrane within the channel of the plunger head, the membrane configured to allow air to pass from the interior volume of the reservoir to an interior volume of the bellows member through the channel of the plunger head, the membrane configured to inhibit fluidic media from passing from the interior volume of the reservoir to the interior volume of the bellows member through the channel of the plunger head in a case where fluidic media is in the interior volume of the reservoir.

In an embodiment for a system for managing air bubbles, the system may include, but is not limited to, a first reservoir, a first plunger head, a second reservoir, a second plunger head, and a membrane. The first reservoir may have an interior volume for containing fluidic media. The first plunger head may be moveable within the first reservoir. The second reservoir may have an interior volume for containing air. The first reservoir and the second reservoir may have a passage connecting the interior volume of the first reservoir and the interior volume of the second reservoir. The second plunger head may be moveable within the second reservoir. The membrane may be for allowing air to pass from the interior volume of the first reservoir to the interior volume of the second reservoir through the passage and for inhibiting fluidic media from passing from the interior volume of the first reservoir to the interior volume of the second reservoir through the passage.

In various embodiments, the first plunger head and the second plunger head may be configured to move substantially simultaneously. In some embodiments, the second plunger head may be operatively connected to the first plunger head.

In various embodiments, the first reservoir may have a septum pierceable by a needle for providing a fluid path between a vial containing fluidic media and the interior volume of the first reservoir. In some embodiments, the first plunger head may be moveable within the first reservoir between at least a first position and a second position. The first plunger head may be for drawing fluidic media from the vial into the interior volume of the first reservoir in a case where the vial is connected to the first reservoir and the first plunger head is moved to the second position of the first plunger head.

In various embodiments, the second plunger head may be moveable within the second reservoir between at least a first position and a second position. The membrane may be configured to allow air to pass from the interior volume of the first reservoir through the passage to the interior volume of the second reservoir in a case where air is in the interior volume of the first reservoir and the second plunger head is moved to the second position of the second plunger head.

In various embodiments, the interior volume of the second reservoir may be located on one side of the second plunger head. The second reservoir may have a chamber on an opposite side of the second plunger head from the interior volume of the second reservoir. The second reservoir may have a port for expelling air from the interior volume of the second reservoir in a case where the interior volume of the second reservoir contains air and the port of the second reservoir and the interior volume of the second reservoir are in communication. In various embodiments, the membrane may comprise a hydrophobic membrane.

A method of making a system for managing air bubbles in accordance with an embodiment of the present invention may include, but is not limited to, (i) providing a first reservoir having an interior volume for containing fluidic media, (ii) locating a first plunger head moveable within the first reservoir, (iii) providing a second reservoir having an interior volume for containing air, the first reservoir and the second reservoir having a passage connecting the interior volume of the first reservoir and the interior volume of the second reservoir, (iv) locating a second plunger head moveable within the second reservoir, and (v) providing a membrane for allowing air to pass from the interior volume of the first reservoir to the interior volume of the second reservoir through the passage and for inhibiting fluidic media from passing from the interior volume of the first reservoir to the interior volume of the second reservoir through the passage.

In an embodiment for a system for managing air bubbles, the system may include, but is not limited to, an outer reservoir, an inner reservoir, a plunger head, and a membrane. The outer reservoir may have an interior volume for containing fluidic media. The inner reservoir may have an interior volume. At least a portion of the inner reservoir may be configured to be moveable in the outer reservoir. The plunger head may be moveable within the inner reservoir. The membrane may be for allowing air to pass from the interior volume of the outer reservoir to the interior volume of the inner reservoir and for inhibiting fluidic media from passing from the interior volume of the outer reservoir to the interior volume of the inner reservoir.

In various embodiments, the plunger head may be moveable within the inner reservoir between at least a first plunger position and a second plunger position. A vacuum in the interior volume of the inner reservoir may be created when the plunger head is moved from the first plunger position to the second plunger position. In some embodiments, the outer reservoir may have a septum pierceable by a needle for providing a fluid path from a vial containing fluidic media to the interior volume of the outer reservoir.

In further embodiments, the inner reservoir may be configured to be moveable in the outer reservoir between at least a first inner reservoir position and a second inner reservoir position. Fluidic media may be drawn from the vial into the interior volume of the outer reservoir in a case where the interior volume of the outer reservoir is in fluid communication with the vial and the inner reservoir is moved from the first inner reservoir position to the second inner reservoir position. In various embodiments, the membrane comprises a hydrophobic filter.

A method of making a system for managing air bubbles in accordance with an embodiment of the present invention may include, but is not limited to, (i) providing an outer reservoir having an interior volume for containing fluidic media, (ii) providing an inner reservoir having an interior volume, at least a portion of the inner reservoir configured to be moveable in the outer reservoir, (iii) locating a plunger head moveable within the inner reservoir, and (iv) providing a membrane for allowing air to pass from the interior volume of the outer reservoir to the interior volume of the inner reservoir and for inhibiting fluidic media from passing from the interior volume of the outer reservoir to the interior volume of the inner reservoir.

In an embodiment for a system for transferring fluidic media, the system may include, but is not limited to, an outer reservoir and an inner reservoir. The outer reservoir may have an interior volume for containing fluidic media. The inner reservoir may have an interior volume. The inner reservoir may have a septum pierceable by a needle. The needle may be for providing a path from a vial containing fluidic media to the interior volume of the inner reservoir in a case where a first end of the needle is in contact with fluidic media in the vial and a second end of the needle opposite the first end of the needle is in the interior volume of the inner reservoir. The outer reservoir may have a septum pierceable by the needle. The needle may be for providing a fluid path from the vial containing fluidic media to the interior volume of the outer reservoir in a case where the first end of the needle is in contact with fluidic media in the vial and the second end of the needle is in the interior volume of the outer reservoir. At least a portion of the inner reservoir may be configured to be moveable in the outer reservoir between at least a first inner reservoir position and a second inner reservoir position In various embodiments, the inner reservoir may be in the first inner reservoir position when the second end of the needle is in the interior volume of the inner reservoir. The inner reservoir may be in the second inner reservoir position when the second end of the needle is in the interior volume of the outer reservoir.

In various embodiments, pressure in the interior volume of the inner reservoir may be substantially equal to pressure in the vial when the inner reservoir is in the first inner reservoir position. In some embodiments, pressure in the vial may be greater than pressure in the interior volume of the outer reservoir when the inner reservoir is in the second inner reservoir position.

A method of making a system for transferring fluidic media in accordance with an embodiment of the present invention may include, but is not limited to, (i) providing an outer reservoir having an interior volume for containing fluidic media, (ii) providing an inner reservoir having an interior volume, the inner reservoir having a septum pierceable by a needle, the needle for providing a path from a vial containing fluidic media to the interior volume of the inner reservoir in a case where a first end of the needle is in contact with fluidic media in the vial and a second end of the needle opposite the first end of the needle is in the interior volume of the inner reservoir, (iii) configuring the outer reservoir to include a septum pierceable by the needle, the needle for providing a fluid path from the vial containing fluidic media to the interior volume of the outer reservoir in a case where the first end of the needle is in contact with fluidic media in the vial and the second end of the needle is in the interior volume of the outer reservoir, and (iv) configuring at least a portion of the inner reservoir to be moveable in the outer reservoir between at least a first inner reservoir position and a second inner reservoir position.

BRIEF DESCRIPTION OF THE DRAWINGS

FIG. 13B illustrates a cross-sectional view of a system for transferring fluidic media in accordance with an embodiment of the present invention.

DETAILED DESCRIPTION OF PREFERRED EMBODIMENTS

Figure 1:
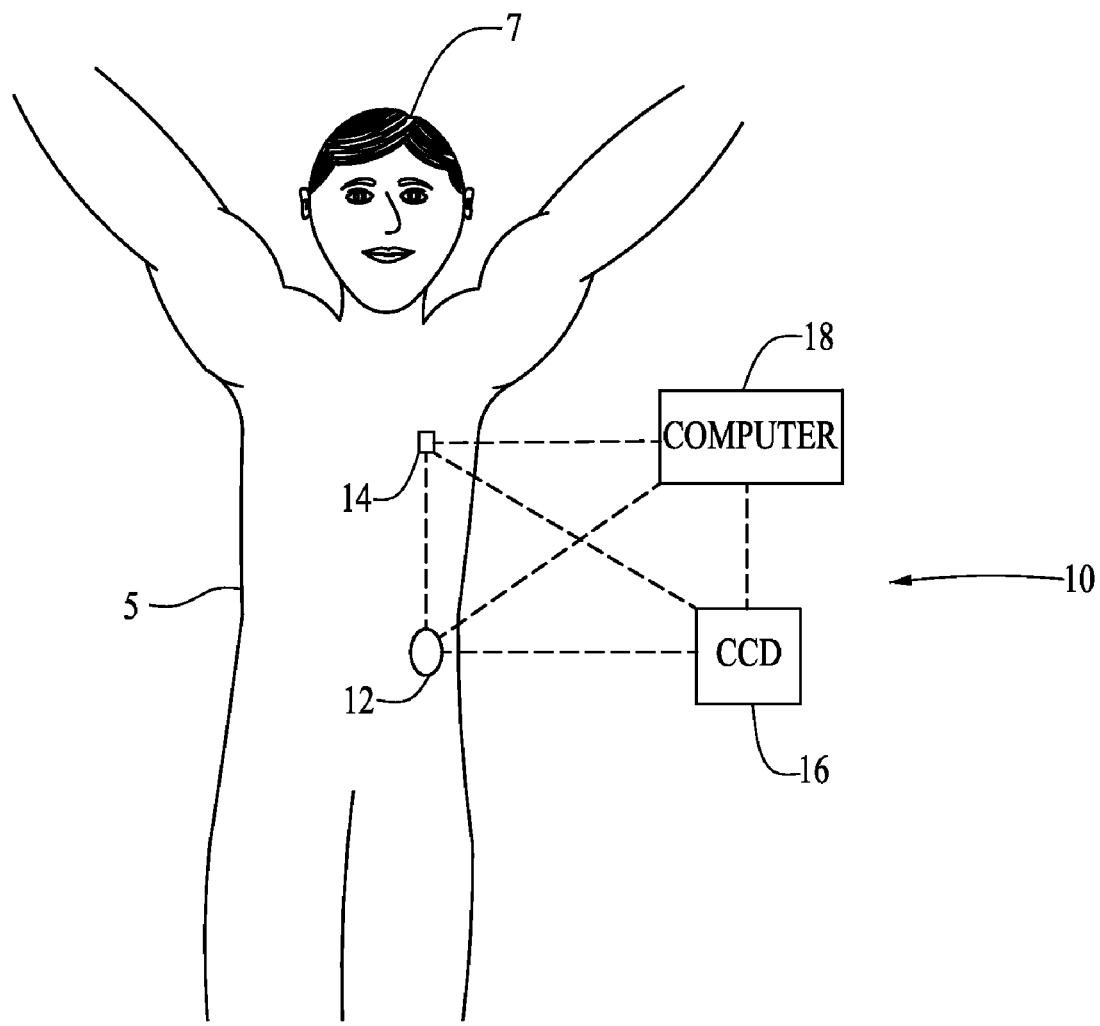
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, delivery device 12, sensing device 14, CCD 16 and computer 18 may be similar to those described in the following U.S. Patent Applications that were assigned to the assignee of the present invention, however, with a reservoir and plunger configuration such as described herein with reference to FIGS. 7-8C, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir". In other embodiments, the system 10, delivery device 12, sensing device 14, CCD 16, and computer 18 may have other suitable configurations.

The delivery device 12 is configured to deliver fluidic media to the body 5 of the user-patient 7. In various embodiments, fluidic media includes a liquid, a fluid, a gel, or the like. In some embodiments, fluidic media includes a medicine or a drug for treating a disease or a medical condition. For example, fluidic media may include insulin for treating diabetes, or may include a drug for treating pain, cancer, a pulmonary disorder, HIV, or the like. In some embodiments, fluidic media includes a nutritional supplement, a dye, a tracing medium, a saline medium, a hydration medium, or the like.

The sensing device 14 includes a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7. In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In other embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. Also, in various embodiments, the delivery device 12 and/or the sensing device 14 may be configured to transmit data to the CCD 16 and/or the computer 18 for display or processing of the data by the CCD 16 and/or the computer 18.

Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same", all of which are incorporated herein by reference in their entirety.

Figure 2:
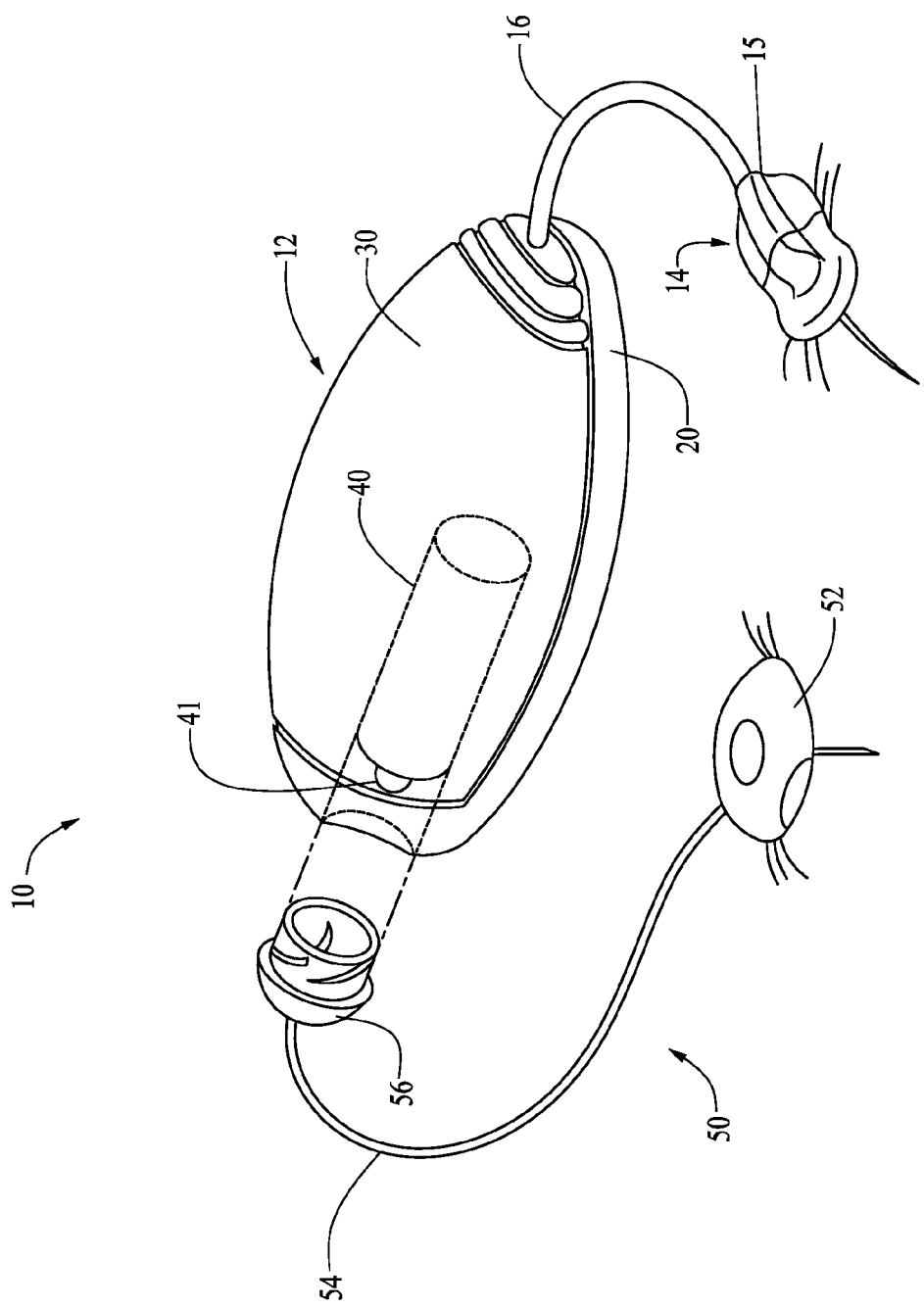
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 supports the reservoir system 40 and has a bottom surface (facing downward and into the page in FIG. 2) that is configured to secure to the body of a user-patient. An adhesive may be employed at an interface between the bottom surface of the disposable housing 20 and the skin of a user-patient, so as to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12 may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 is configured for containing or holding fluidic media, such as, but not limited to insulin. In various embodiments, the reservoir system 40 includes a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 is able to be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 includes a port 41 for allowing fluidic media to flow into and/or flow out of the interior volume of the reservoir system 40. In some embodiments, the infusion path 50 includes a connector 56, a tube 54, and a needle apparatus 52. The connector 56 of the infusion path 50 may be connectable to the port 41 of the reservoir system 40. In various embodiments, the disposable housing 20 is configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 is covered with or supports a septum (not shown in FIG. 2), such as a self-sealing septum, or the like. The septum may be configured to prevent fluidic media from flowing out of the reservoir system 40 through the port 41 when the septum is not pierced. Also, in various embodiments, the connector 56 of the infusion path 50 includes a needle for piercing the septum covering the port 41 of the reservoir system 40 so as to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector", which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user-patient. Also, in various embodiments, the tube 54 connects the connector 56 with the needle apparatus 52 and is hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, so as to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction so as to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. Also, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 16 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 includes a sensor 15 connected by the connection element 16 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
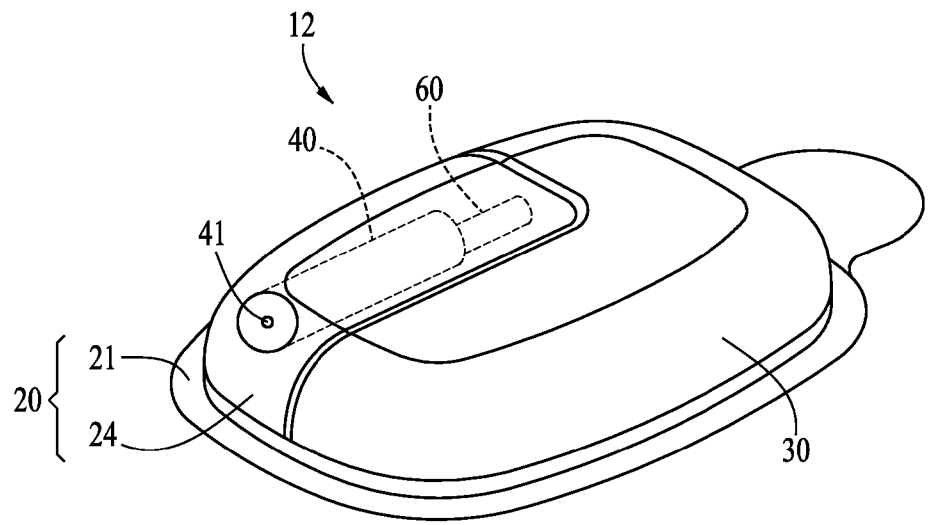
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user-patient. The reservoir retaining portion 24 of the disposable housing 20 is configured to house the reservoir system 40. The reservoir retaining portion 24 of the disposable housing 20 may be configured to have an opening to allow for the port 41 of the reservoir system 40 to be accessed from outside of the reservoir retaining portion 24 while the reservoir system 40 is housed in the reservoir retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
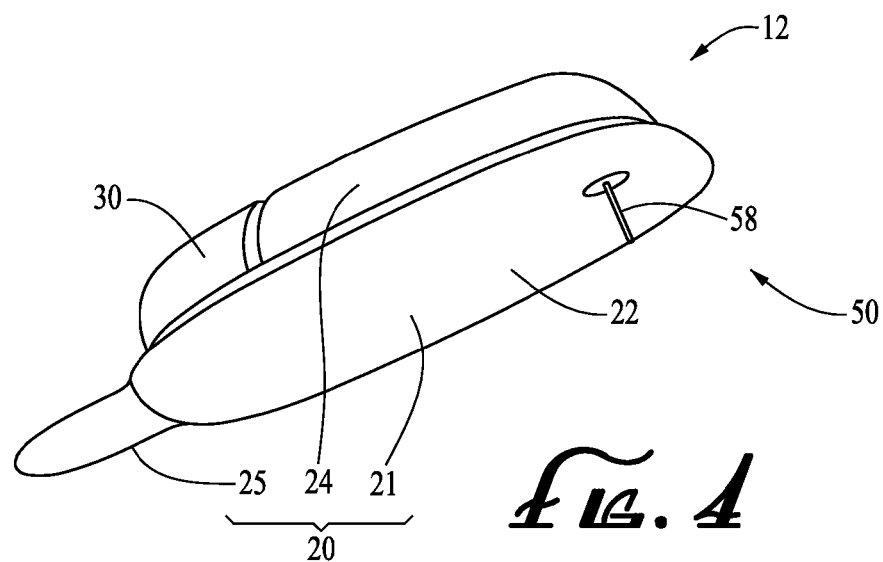
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
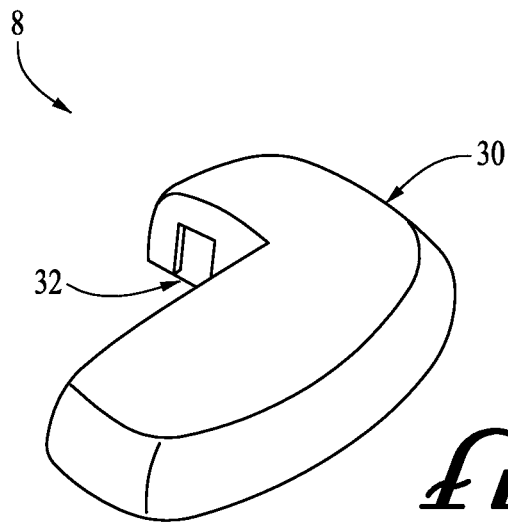
FIG. 5A illustrates a durable portion of a delivery device in accordance with an embodiment of the present invention.
Figure 5B:
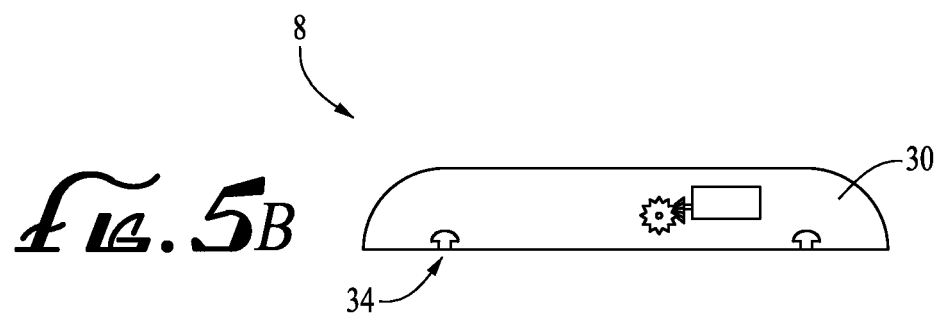
FIG. 5B illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention.

Figure 5C:
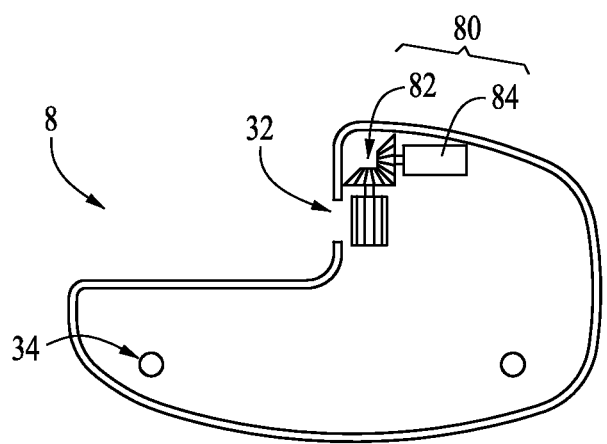
FIG. 5C illustrates a section view of a durable portion of a delivery device in accordance with an embodiment of the present invention.

FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). Also, in various embodiments, the durable housing 30 is configured with an opening 32 for receiving a plunger arm 60 (refer to FIG. 3). Also, in various embodiments, the durable housing 30 may include one or more connection members 34, such as tabs, insertion holes, or the like, for connecting with the base 21 of the disposable housing 20 (refer to FIG. 3).

Figure 6A:
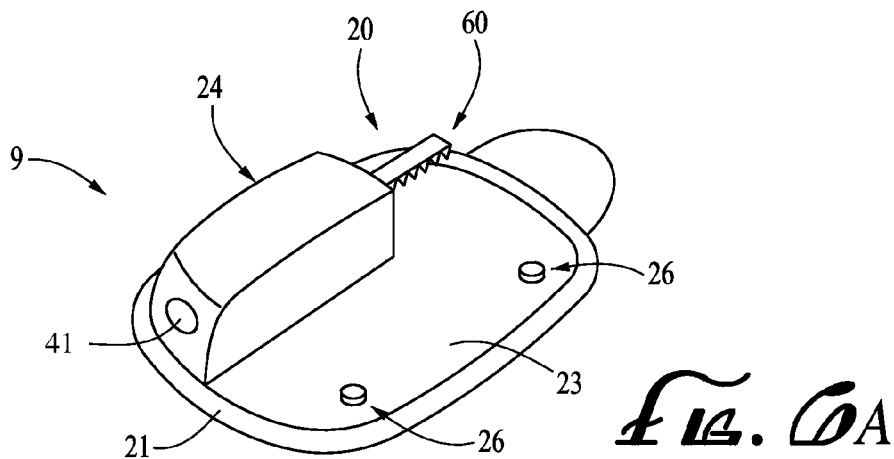
FIG. 6A illustrates a disposable portion of a delivery device in accordance with an embodiment of the present invention.
Figure 6B:
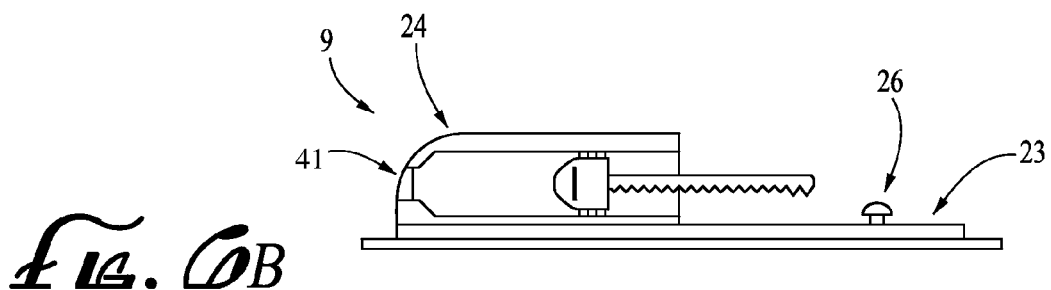
FIG. 6B illustrates a section view of a disposable portion of a delivery device in accordance with an embodiment of the present invention.
Figure 6C:
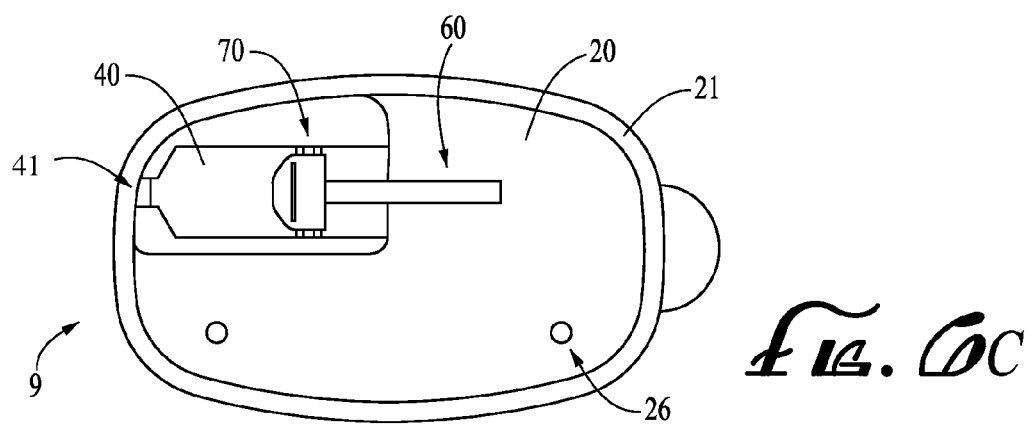
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 includes the base 21 and the reservoir retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 is housed within the reservoir retaining portion 24 of the disposable housing 20, and the reservoir system 40 is configured to hold fluidic media. Also, in various embodiments, the plunger head 70 is disposed at least partially within the reservoir system 40 and is moveable within the reservoir system 40 to allow fluidic media to fill into the reservoir system 40 and to force fluidic media out of the reservoir system 40. In some embodiments, the plunger arm 60 is connected to or is connectable to the plunger head 70.

Also, in some embodiments, a portion of the plunger arm 60 extends to outside of the reservoir retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, a user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. Also, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir system 40 includes reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 includes the reservoir status circuitry (not shown), and the reservoir status circuitry is configured to read data from the reservoir circuitry when the reservoir system 40 is inserted into the disposable portion 9.

In various embodiments, the reservoir status circuitry is further configured to store data to the reservoir circuitry after at least some of the contents of the reservoir system 40 have been transferred out of the reservoir system 40, so as to update information in the reservoir circuitry related to an amount of contents still remaining in the reservoir system 40. In some embodiments, the reservoir status circuitry is configured to store data to the reservoir circuitry, so as to update information in the reservoir circuitry related to an amount of contents still remaining in the reservoir system 40, when the reservoir system 40 is inserted into the disposable portion 9. In some embodiments, the delivery device 12 includes the reservoir status circuitry (not shown) and the reservoir system 40 includes the reservoir circuitry (not shown), and the reservoir status circuitry selectively inhibits use of the delivery device 12 or selectively provides a warning signal based on information read by the reservoir status circuitry from the reservoir circuitry.

Figure 7:
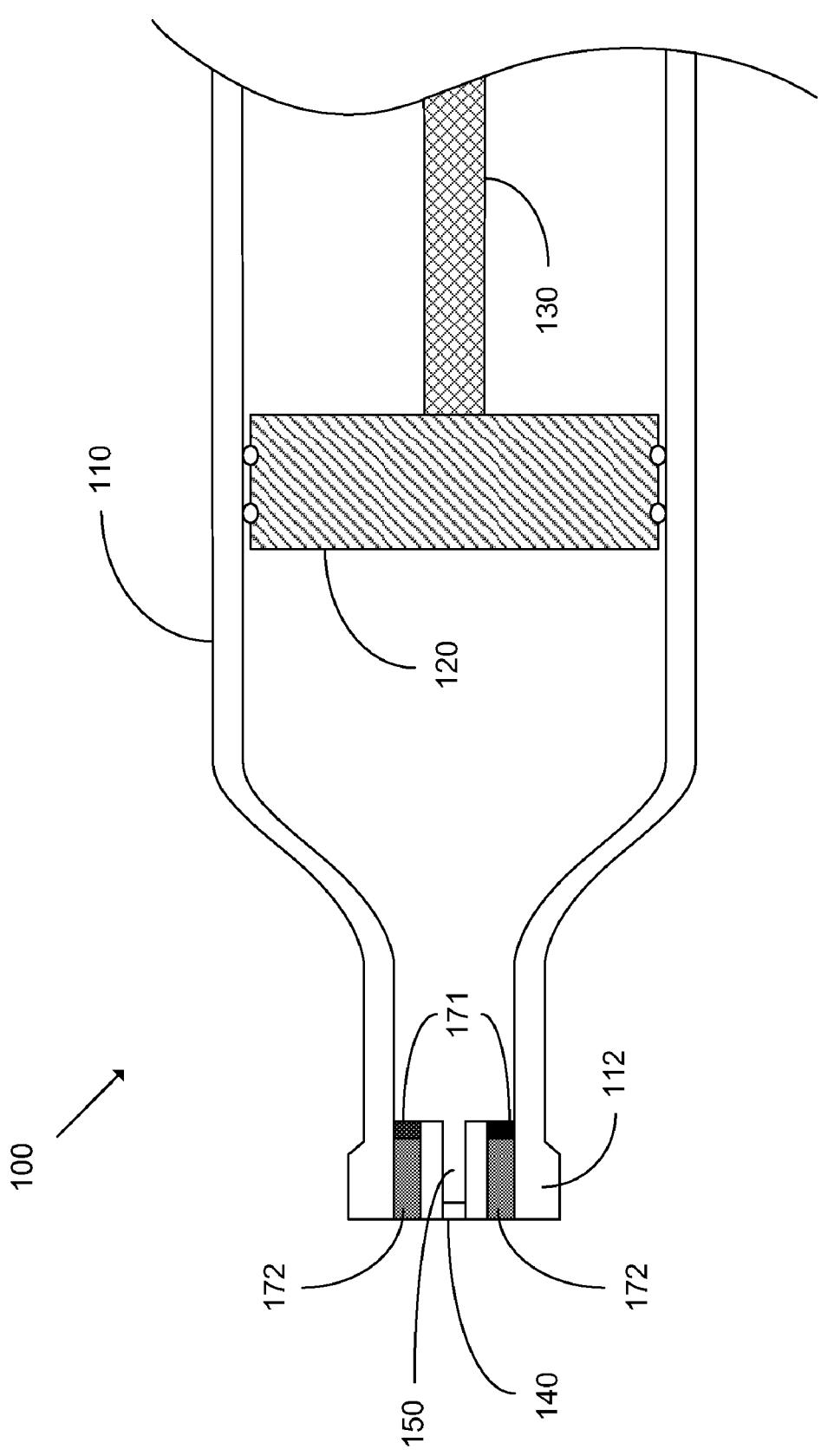
FIG. 7 illustrates a cross-sectional view of a system for managing air bubbles in accordance with an embodiment of the present invention.

FIG. 7 illustrates a cross-sectional view of a system 100 in accordance with an embodiment of the present invention. The system 100 may include, but is not limited to, a reservoir 110, a plunger head 120, a plunger arm 130, a septum 140, one or more hydrophobic filters 171, and one or more air passages 172. The reservoir 110 may have a hollow interior for containing fluidic media. The plunger head 120 may be located within the reservoir 110 and may be moveable in an axial direction of the reservoir 110 to expand or contract an interior volume of the reservoir 110. The reservoir may include a neck portion 112. The septum 140 may be located at an end of the neck portion 112 of the reservoir 110. A fluid channel 150 may be defined in the neck portion 112 of the reservoir 110 extending from the septum 140.

The one or more air passages 172 may extend from within the reservoir 110 to a same outer surface of the reservoir 110 through which fluidic media is expelled from the reservoir 110. In various embodiments, the one or more air passages 172 may surround the fluid channel 150. The one or more hydrophobic filters 171 may be located at ends of the one or more air passages 172 within the reservoir 110. The hydrophobic filters 171 may comprise hydrophobic material that may substantially prevent fluidic media in the reservoir 110 from entering the one or more air passages 172. The one or more air passages 172 may allow for air in the reservoir to pass through the one or more hydrophobic filters 171 and to exit the reservoir 110.

A method in accordance with the present invention allows for expelling fluidic media from the reservoir 110. In a first step of the method, a fluid path may be established through the septum 140 to the fluid channel 150. In a second step of the method, the plunger head 120 may be depressed within the reservoir 110, such that fluidic media is expelled through the fluid channel 150 and out of the reservoir 110 through the septum 140.

When fluidic media is being expelled through the fluid channel 150, air in the reservoir 110 may be able to pass through the one or more hydrophobic filters 171 and out of the reservoir 110 through the one or more air passages 172. Fluidic media may be substantially prevented from entering the one or more air passages 172 by the one or more hydrophobic filters 171. Thus, in accordance with the method, fluidic media may be expelled from the reservoir 110 while air in the reservoir 110 is able to escape through the one or more air passages 172 that exit the reservoir 110 on a same side of the reservoir 110 that fluidic media exits the reservoir 110.

Figure 8:
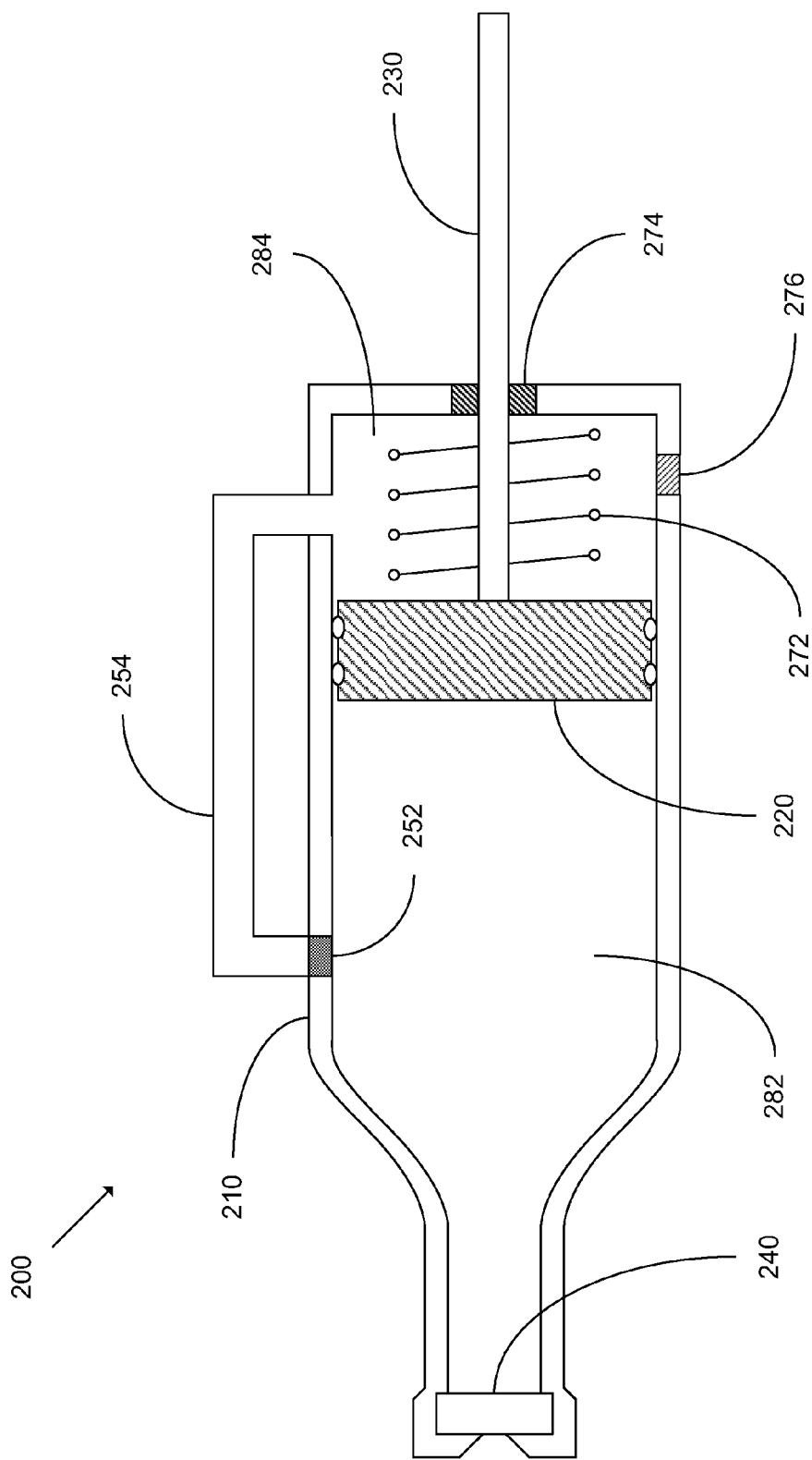
FIG. 8 illustrates a cross-sectional view of a system for managing air bubbles in accordance with an embodiment of the present invention.

FIG. 8 illustrates a cross-sectional view of a system 200 in accordance with an embodiment of the present invention. The system 200 may include, but is not limited to, a reservoir 210, a plunger head 220, a plunger arm 230, a septum 240, a membrane 252, a channel 254, a bias member, such as a spring 272, a seal 274, and a valve 276. The reservoir 210 may have a interior volume 282 for containing fluidic media between the plunger head 220 and the septum 240. The reservoir 210 may have a chamber 284 on an opposite side of the plunger head 220 from the interior volume 282 of the reservoir 210.

The plunger head 220 may be advanced within the reservoir 210 to expel fluidic media from the reservoir 210. The spring 272 may be connected between a surface of the reservoir 210 and the plunger head 220 in the chamber 284 of the reservoir 210. The seal 274 may create a substantially airtight seal around the plunger arm 230 in a location where the plunger arm 230 exits the chamber 284 of the reservoir 210. The valve 276 may allow a vacuum to be applied to the chamber 284. The membrane 252 may be located in an opening in a wall of the reservoir 210 and air may be able to pass from the interior volume 282 of the reservoir 210 through the membrane 252 and through the channel 254 of the reservoir 210 into the chamber 284 of the reservoir 210. The membrane 252 may comprise, for example, a hydrophobic material, or the like.

In some embodiments, a vacuum may be applied to the chamber 284 of the reservoir 210 through the valve 276 to create a vacuum in the chamber 284 of the reservoir 210, and then the valve 276 may be closed. The membrane 252 and the channel 254 of the reservoir 210 may allow for a transfer of air bubbles from a fluidic media side of the plunger head 220 to a back side of the plunger head 220. The membrane 252 may substantially prevent a loss of fluidic media through the channel 254 of the reservoir 210. A slight vacuum in the chamber 284 of the reservoir 210 and an advancement of the plunger head 220 by the spring 272 may promote a migration of air bubbles from the interior volume 282 of the reservoir 210 to the chamber 284 of the reservoir 210 through the channel 254 of the reservoir 210.

Thus, embodiments of the present invention may allow for a vacuum in a chamber of a reservoir behind a plunger head to pull or otherwise draw air out of an interior volume of the reservoir through a channel of the reservoir from the interior volume of the reservoir to the chamber of the reservoir. Such embodiments may allow for continuous degassing of fluidic media in the interior volume of the reservoir.

Figure 9:
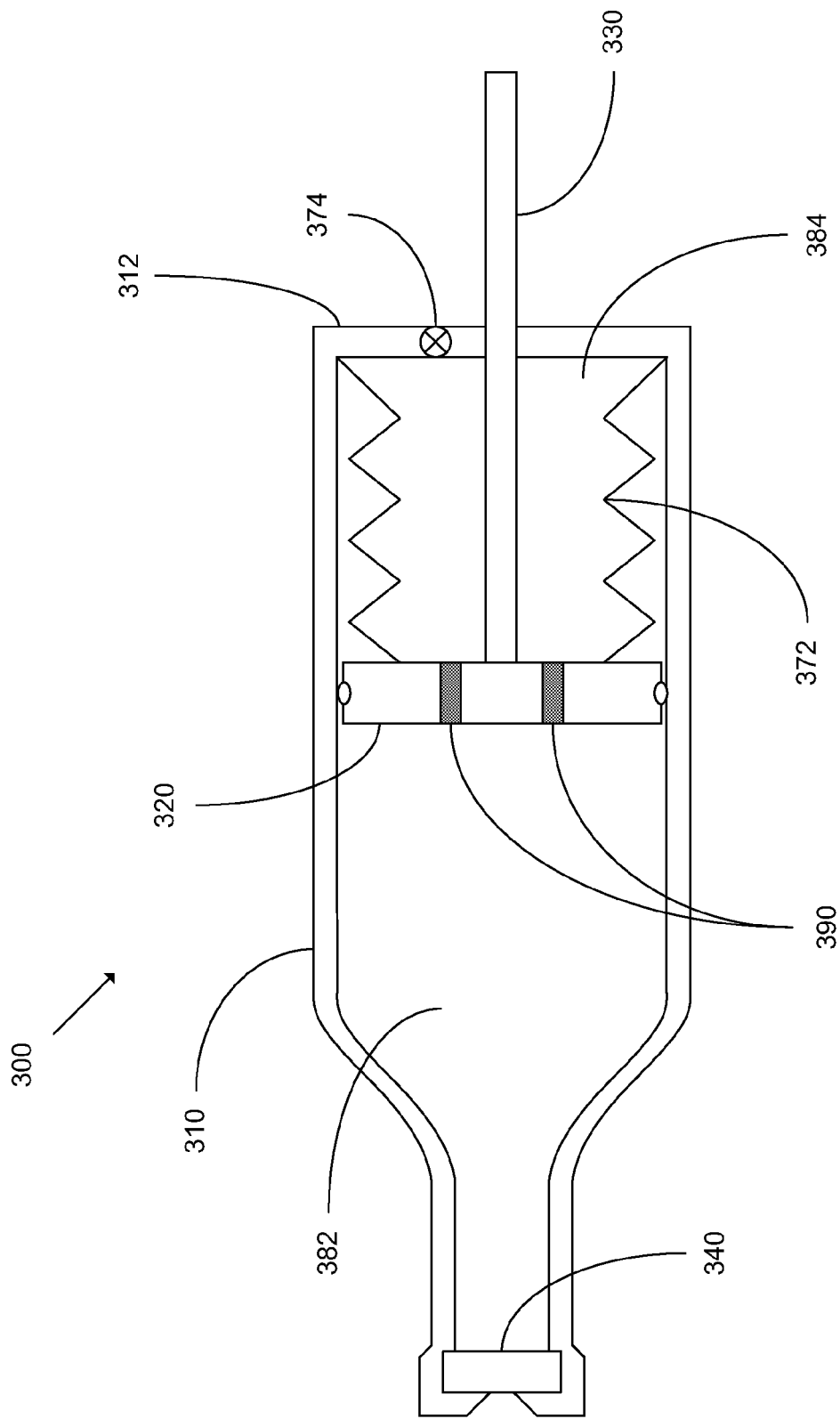
FIG. 9 illustrates a cross-sectional view of a system for managing air bubbles in accordance with an embodiment of the present invention.

FIG. 9 illustrates a cross-sectional view of a system 300 in accordance with an embodiment of the present invention. The system 300 may include, but is not limited to, a reservoir 310, a plunger head 320, a plunger arm 330, a septum 340, a bellows member 372, a one-way valve 374, and one or more membranes 390. The plunger head 320 may be connected to the plunger arm 330, and the plunger head 320 may be moveable within the reservoir 310. The reservoir 310 may have an interior volume 382 for containing fluidic media between the plunger head 320 and the septum 340. The septum 340 may be located at an exit port of the reservoir 310.

The bellows member 372 may be connected between a back surface 312 of the reservoir 310 and the plunger head 320. The bellows member 372 may be connected to a backside of the plunger head 320 opposite from a side of the plunger head 320 that contacts fluidic media. The bellows member 372 may be sealed to the plunger head 320. The one or more membranes 390 may be located on the side of the plunger head 320 in contact with fluidic media. The one or more membranes 390 may lead to channels through the plunger head 320 that extend from the side of the plunger head 320 in contact with fluidic media to the backside of the plunger head 320.

The one or more membranes 390 may comprise, for example, a hydrophobic material, or the like, that allows air to pass through, but may substantially prevent a passage of fluidic media through the one or more membranes 390. Thus, air may be able to pass from the interior volume 382 of the reservoir 310 through the one or more membranes 390 and through the plunger head 320 into an area 384 within the bellows member 372. The bellows member 372 may be able to expand or contract with a movement of the plunger head 320. As the plunger head 320 is moved forward to deliver fluidic media, a vacuum may be generated in the bellows member 372 and, thus, air bubbles, vapor, or the like may be drawn through the one or more membranes 390 and into the area 384 within the bellows member 372. When the reservoir 310 is completely filled, the bellows member 372 may be fully compressed, and the air in the bellows member 372 may be forced through the one-way valve 374.

Figure 10A:
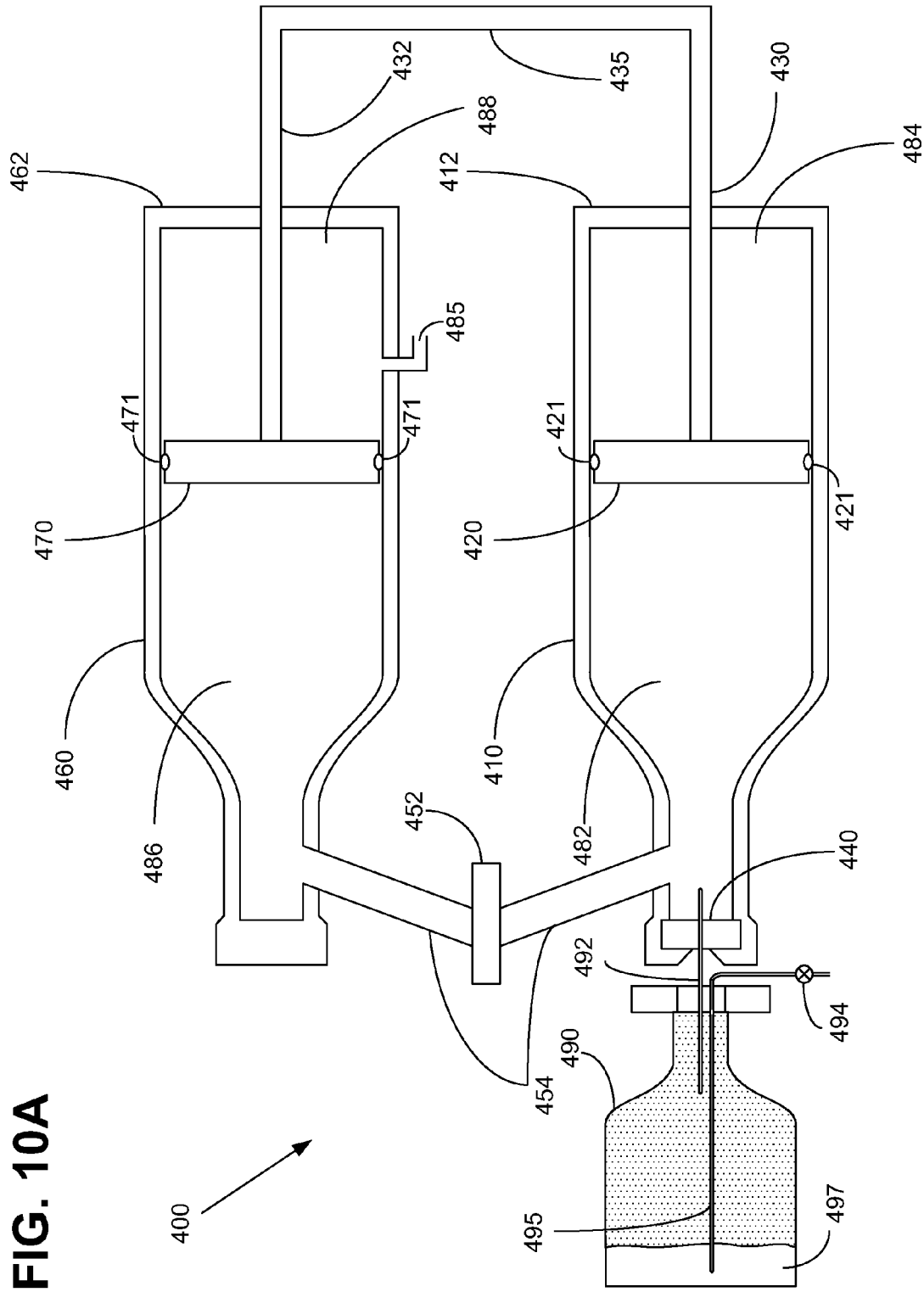
FIG. 10A illustrates a cross-sectional view of a system for managing air bubbles in accordance with an embodiment of the present invention.
Figure 10B:
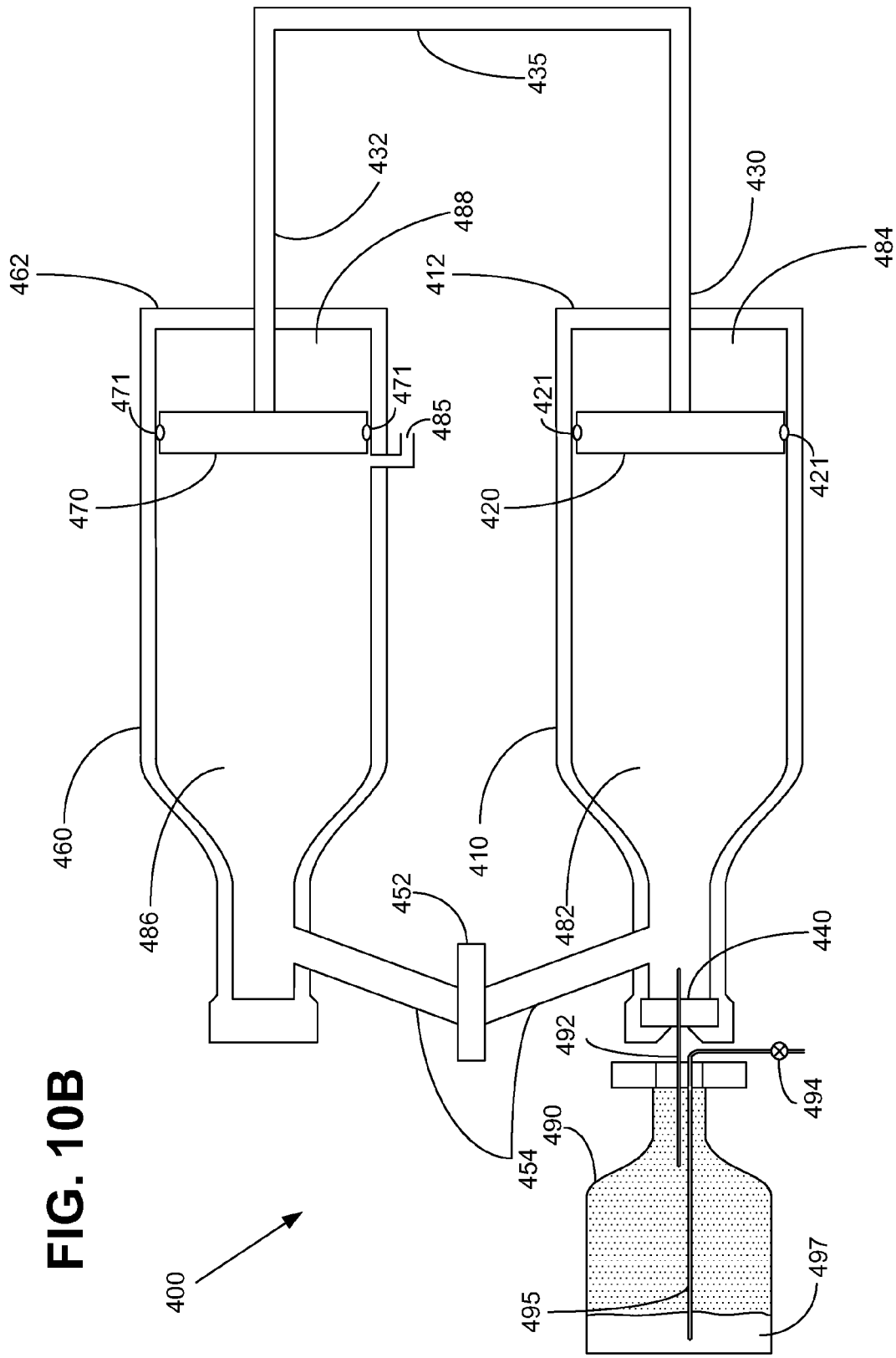
FIG. 10B illustrates a cross-sectional view of a system for managing air bubbles in accordance with an embodiment of the present invention.

FIGS. 10A and 10B illustrate a cross-sectional view of a system 400 in accordance with an embodiment of the present invention. The system 400 may include, but is not limited to, a first reservoir 410, a first plunger head 420, a second reservoir 460, a second plunger head 470, and a membrane 452. The first plunger head 420 may be positioned within the first reservoir 410. The second plunger head 470 may be positioned within the second reservoir 460.

The first reservoir 410 may have a septum 440. The first reservoir 410 may have an interior volume 482 for containing fluidic media on one side of the first plunger head 420. The first reservoir 410 may have a first chamber 484 on an opposite side of the first plunger head 420 from the interior volume 482 of the first reservoir 410.

The second reservoir 460 may have an interior volume 486 on one side of the second plunger head 470. The interior volume 486 of the second reservoir 460 may be for, but is not limited to, containing air, or the like. The second reservoir 460 may have a second chamber 488 on an opposite side of the second plunger head 470 from the interior volume 486 of the second reservoir 460.

The first plunger head 420 may be moveable in an axial direction within the first reservoir 410 to expand or contract the interior volume 482 of the first reservoir 410. Accordingly, a volume of the first chamber 484 of the first reservoir 410 may contract while the interior volume 482 of the first reservoir 410 expands. The second plunger head 470 may be moveable in an axial direction within the second reservoir 460 to expand or contract the interior volume 486 of the second reservoir 460. Accordingly, a volume of the second chamber 488 of the second reservoir 460 may contract while the interior volume 486 of the second reservoir 460 expands.

The first plunger head 420 may be connected to an end of a first plunger arm 430. The second plunger head 470 may be connected to an end of a second plunger arm 432. The opposite ends of the first plunger arm 430 and the second plunger arm 432 connected to the first plunger head 420 and the second plunger head 470, respectively, may be operatively connected to each other, for example by a handle 435. In some embodiments, this may allow the first plunger head 420 and the second plunger head 470 to be moved substantially simultaneously to one another.

The first reservoir 410 and the second reservoir 460 may have a passage 454 connecting the interior volume 482 of the first reservoir 410 and the interior volume 486 of the second reservoir 460. The membrane 452 may be positioned in the passage 454. The membrane 452 may be configured such that air may be able to pass from the interior volume 482 of the first reservoir 410 through the passage 454 and the membrane 452 into the interior volume 486 of the second reservoir 460. The membrane 452 may comprise, for example, a hydrophobic material, or the like.

The system 400 may include a vial 490 and a needle 492. The vial 490 may be for containing fluidic media. The septum 440 of the first reservoir 410 may be pierceable by the needle 492 to provide a fluid path between the vial 490 and the interior volume 482 of the first reservoir 410. Fluidic media may be drawn from the vial 490 through the needle 492 to the interior volume 482 of the first reservoir 410 in a case where the vial 490 is connected to the first reservoir 410 and the first plunger head 420 is moved within the first reservoir 410, for example away from the septum 440 of the first reservoir 410. The first plunger head 420 may be moved within the first reservoir 410 to draw fluidic media from the vial 490, for example, by pulling on the handle 435.

Similarly, the second plunger head 470 may be moved within the second reservoir 460, for example by pulling on the handle 435. In various embodiments, the first plunger head 420 and the second plunger head 470 may be configured to be moved simultaneously. Thus, for example, in such embodiments, the first plunger head 420 and the second plunger head 470 may be moved within the first reservoir 410 and the second reservoir 470, respectively, by pulling on the handle 435.

In some embodiments, when the handle 435 is pulled to draw fluidic media from the vial 490 to the interior volume 482 of the first reservoir 410, the membrane 452 and the passage 454 may allow for a transfer of air bubbles from the interior volume 482 of the first reservoir 410 to the interior volume 486 of the second reservoir 460. The membrane 452 may substantially prevent a loss of fluidic media from the interior volume 486 of the first reservoir 410 through the passage 454.

In some embodiments, the system 400 may include a second needle 495. An end of the second needle 495 may be located within a headspace 497 of the vial 490 above fluidic media within the vial 490 in a case where the vial 490 is connected to the first reservoir 410 and the vial 490 is inverted. In other embodiments, the end of the second needle 495 may be in contact with fluidic media within the vial 490 in a case where the vial 490 is connected to the first reservoir 410.

An other end of the second needle 495 may be connected to a check valve 494, such as a one-way valve, or the like. The check valve 494 may allow air to enter the vial 490 through the second needle 495. In some embodiments, the check valve 494 may substantially prevent fluidic media from coming out of the vial 490 through the second needle 495 and/or the check valve 494. In various embodiments, the second needle 495 may allow for venting the headspace 497 and/or the vial 490 to atmosphere to facilitate transfer of fluidic media from the vial 490 to the interior volume 482 of the first reservoir 410.

In some embodiments, the second reservoir 460 may have a port 485 for expelling air from the interior volume 486 of the second reservoir 460. Air in the interior volume 486 of the second reservoir 460 may be expelled out the port 485 of the second reservoir 460 in a case where the interior volume 486 of the second reservoir 460 contains air and the interior volume 486 of the second reservoir 460 is in communication with the port 485 of the second reservoir 460. The port 485 of the second reservoir 460 may be in communication with the interior volume 486 of the second reservoir 460 for example when the second plunger head 470 has been sufficiently moved within the second reservoir 460, an example of which is illustrated in FIG. 10B.

Figure 11A:
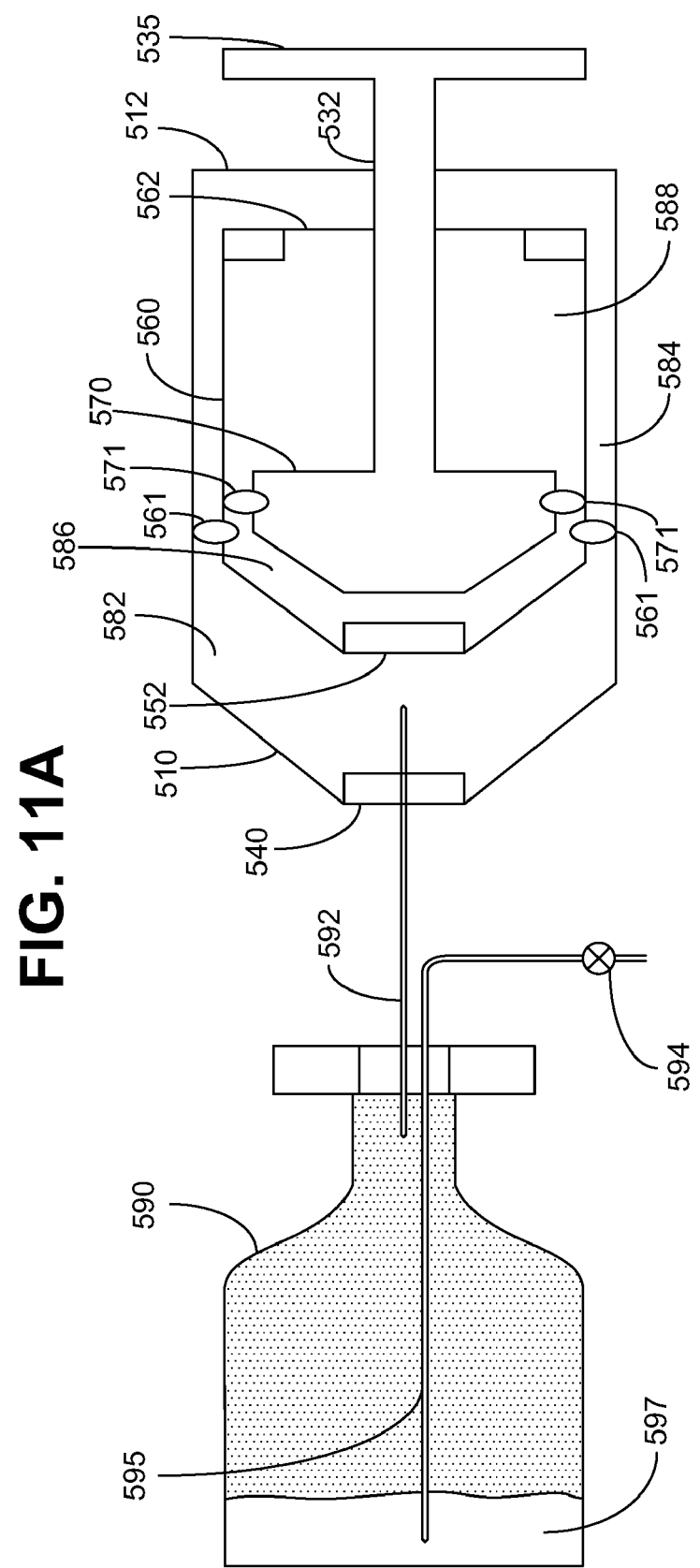
FIG. 11A illustrates a cross-sectional view of a system for managing air bubbles in accordance with an embodiment of the present invention.
Figure 11B:
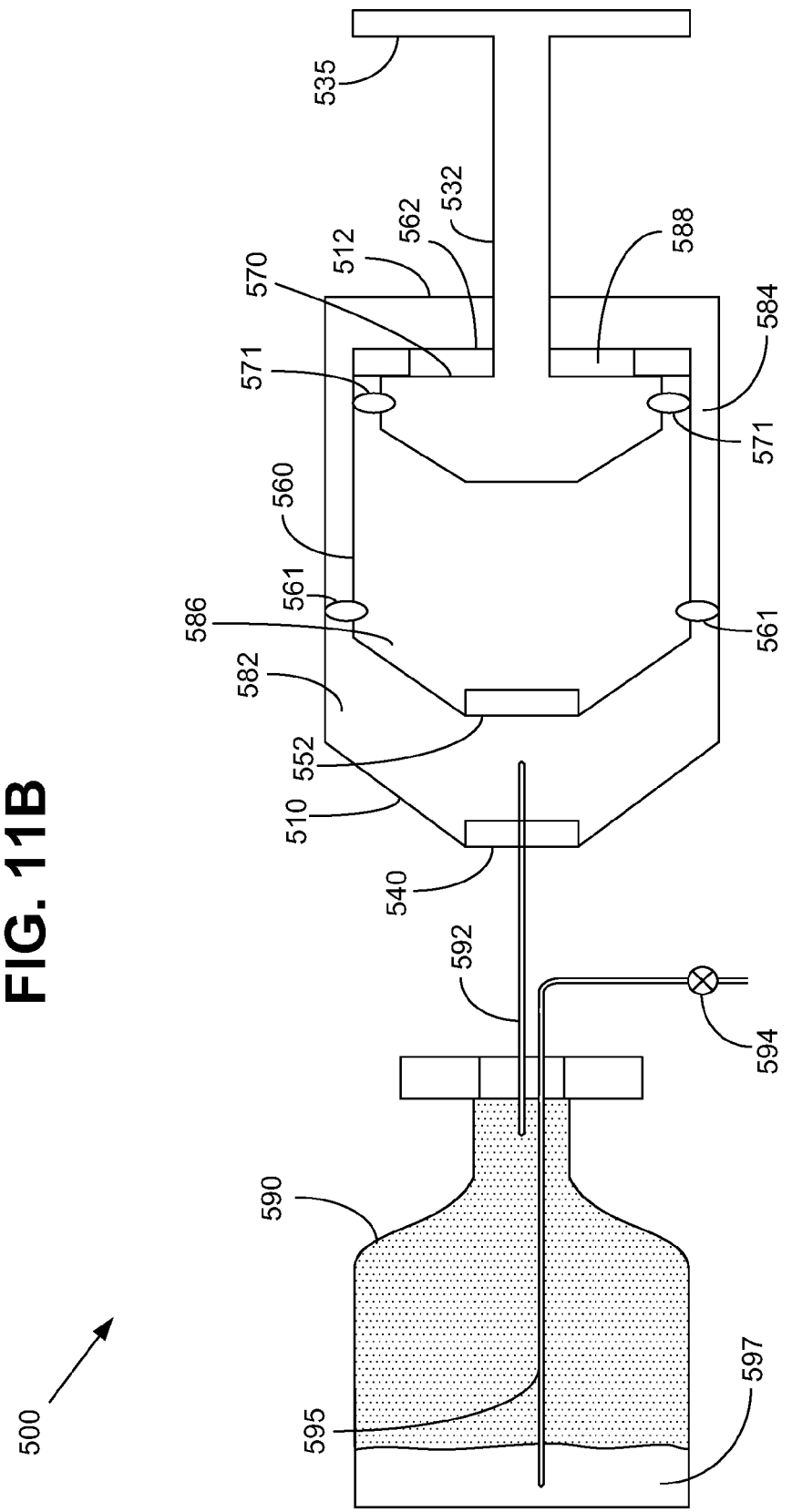
FIG. 11B illustrates a cross-sectional view of a system for managing air bubbles in accordance with an embodiment of the present invention.
Figure 11C:
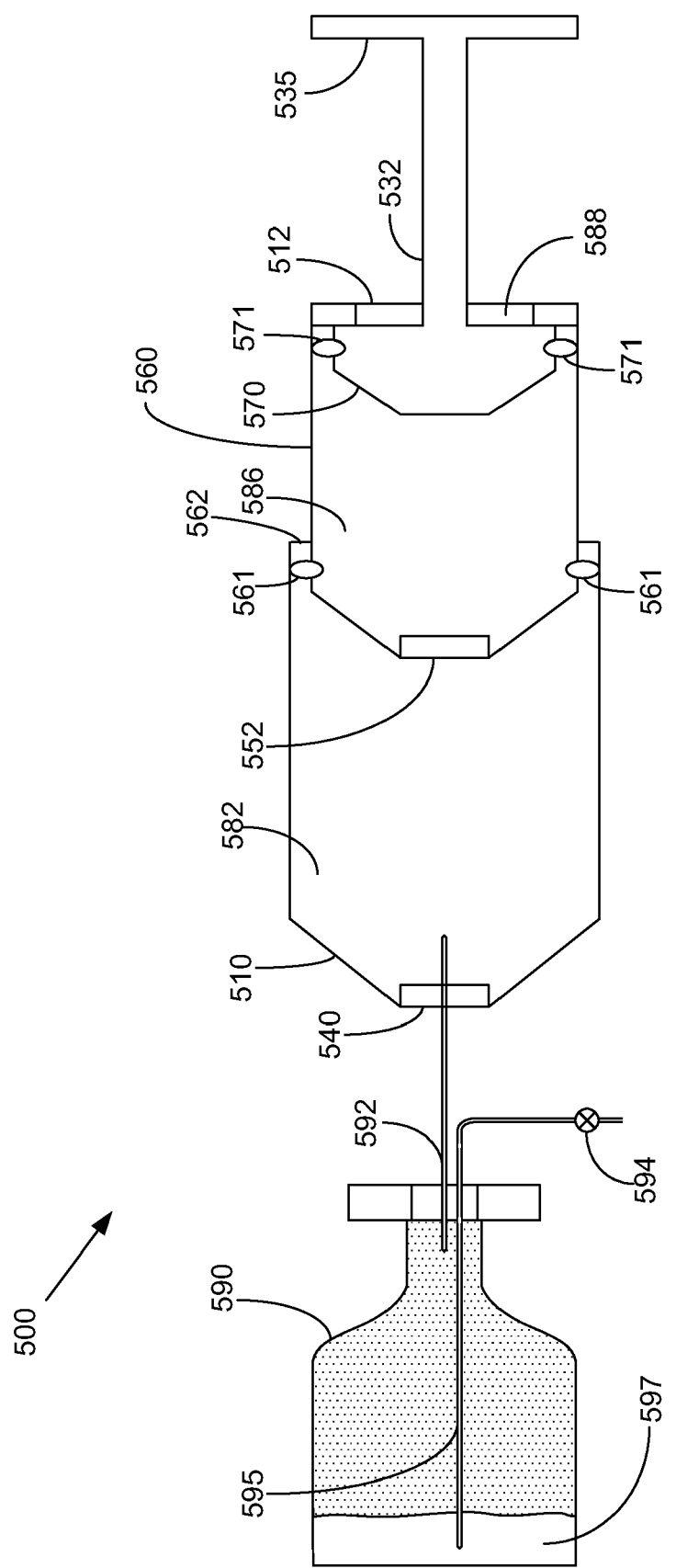
FIG. 11C illustrates a cross-sectional view of a system for managing air bubbles in accordance with an embodiment of the present invention.

FIGS. 11A-11C illustrate a cross-sectional view of a system 500 in accordance with an embodiment of the present invention. The system 500 may include, but is not limited to, an outer reservoir 510, an inner reservoir 560, a plunger head 570, a plunger arm 532, and a handle 535. The outer reservoir 510 may include a septum 540. The outer reservoir 510 may have an interior volume 582 for containing fluidic media. The inner reservoir 560 may be configured to be moveable in an axial direction within the outer reservoir 510 to expand or contract the interior volume 582 of the outer reservoir 510. The inner reservoir 560 may include a membrane 552. The inner reservoir 560 may have an interior volume 586 that may be for containing a gas, such as, but is not limited to, air, or the like.

The plunger head 570 may be configured to be moveable in an axial direction within the inner reservoir 560 to expand or contract the interior volume 586 of the inner reservoir 560. The plunger head 570 may be connected to an end of the plunger arm 532. The plunger arm 532 may extend through a back end 562 of the inner reservoir 560 and a back end 512 of the outer reservoir 510 such that an end of the plunger arm 532 opposite from the end of the plunger arm 532 connected to the plunger head 570 may be connected to the handle 535. The handle 535 may be for moving at least one of the plunger head 570 and the inner reservoir 560.

A seal member 561, such as an o-ring, may be positioned between the inner reservoir 560 and the outer reservoir 510. The interior volume 582 of the outer reservoir 510 may be on one side of the seal member 561. The outer reservoir 510 may have a chamber 584 located on an opposite side of the seal member 561 from the interior volume 582 of the outer reservoir 510. The seal member 561 may be for substantially preventing fluidic media from flowing from the interior volume 582 of the outer reservoir 510 to the chamber 584 of the outer reservoir 510.

A seal member 571, such as an o-ring, may be positioned between the inner reservoir 560 and the plunger head 570. The interior volume 586 of the inner reservoir 560 may be on one side of the seal member 571. The inner reservoir 560 may have a chamber 588 located on an opposite side of the seal member 571 from the interior volume 586 of the inner reservoir 560. The seal member 571 may be for substantially preventing fluidic media from flowing from the interior volume 586 of the inner reservoir 560 to the chamber 588 of the inner reservoir 560.

The membrane 552 may be configured such that air may be able to pass from the interior volume 582 of the outer reservoir 510 through the membrane 552 into the interior volume 586 of the second reservoir 560. Air may be able to pass through the membrane 552 in a case where fluidic media is in the interior volume 582 of the outer reservoir 510 and at least one of the inner reservoir 560 and the plunger head 570 are moved away from the vial 590.

In some embodiments, when the handle 535 is pulled to draw fluidic media from the vial 590 to the interior volume 582 of the first reservoir 510, the membrane 552 may allow for a transfer of air bubbles from the interior volume 582 of the first reservoir 510 to the interior volume 586 of the second reservoir 560. The membrane 552 may substantially prevent a loss of fluidic media between the interior volume 582 of the first reservoir 510 and the interior volume 586 of the second reservoir 560. The membrane 552 may comprise, for example, a hydrophobic material, or the like.

The system 500 may include a vial 590 and a needle 592. The vial 590 may be for containing fluidic media. The septum 540 of the outer reservoir 510 may be pierceable by the needle 592 to provide a fluid path between the vial 590 and the interior volume 582 of the outer reservoir 510.

In some embodiments, the system 500 may include a second needle 595. An end of the second needle 595 may be located within a headspace 597 of the vial 590 above fluidic media within the vial 590 in a case where the vial 590 is connected to the outer reservoir 510 and the vial 590 is inverted. In other embodiments, the end of the second needle 595 may be in contact with fluidic media within the vial 590 in a case where the vial 590 is connected to the outer reservoir 510.

Another end of the second needle 595 may be connected to a check valve 594, such as a one-way valve, or the like. The check valve 594 may allow air to enter the vial 590 through the second needle 595. In some embodiments, the check valve 594 may substantially prevent fluidic media from coming out of the vial 590 through the second needle 595 and/or the check valve 594. In various embodiments, the second needle 595 may allow for venting the headspace 597 or the vial 590 to atmosphere to facilitate the transfer of fluidic media from the vial 590 to the interior volume 582 of the outer reservoir 510.

In operation of the system 500, according to one embodiment of the present invention, the vial 590 may be connected to the outer reservoir 510 by way of the needle 592. The needle 592 may pierce the septum 540 of the outer reservoir 510 to establish a fluid path between the vial 590 and the interior volume 582 of the outer reservoir 510. Once the vial 590 is connected to the outer reservoir 510, the handle 535 may be pulled, for example away from the vial 590, to move the plunger head 570 within the inner reservoir 560. As the plunger head 560 moves within the inner reservoir 560, for example away from the vial 590, the interior volume 586 of the inner reservoir 560 may increase, which may create a vacuum within the interior volume 586 of the inner reservoir 560. The plunger head 570 may be moved within the inner reservoir 560 until the plunger head 570 contacts the back end 562 of the inner reservoir 560 as illustrated in FIG. 11B.

Once the plunger head 570 contacts the back end 562 of the inner reservoir 560, further movement of the handle 535, for example away from the vial 590, may move the inner reservoir 560 within the outer reservoir 510 away from the vial 590 as illustrated in FIG. 11C. This may draw fluidic media from the vial 590 through the needle 592 into the interior volume 582 of the outer reservoir 510. Air bubbles present in fluidic media in the interior volume 582 of the outer reservoir 510 may pass through the membrane 552 into the interior volume 586 of the inner reservoir 560.

Figure 12A:
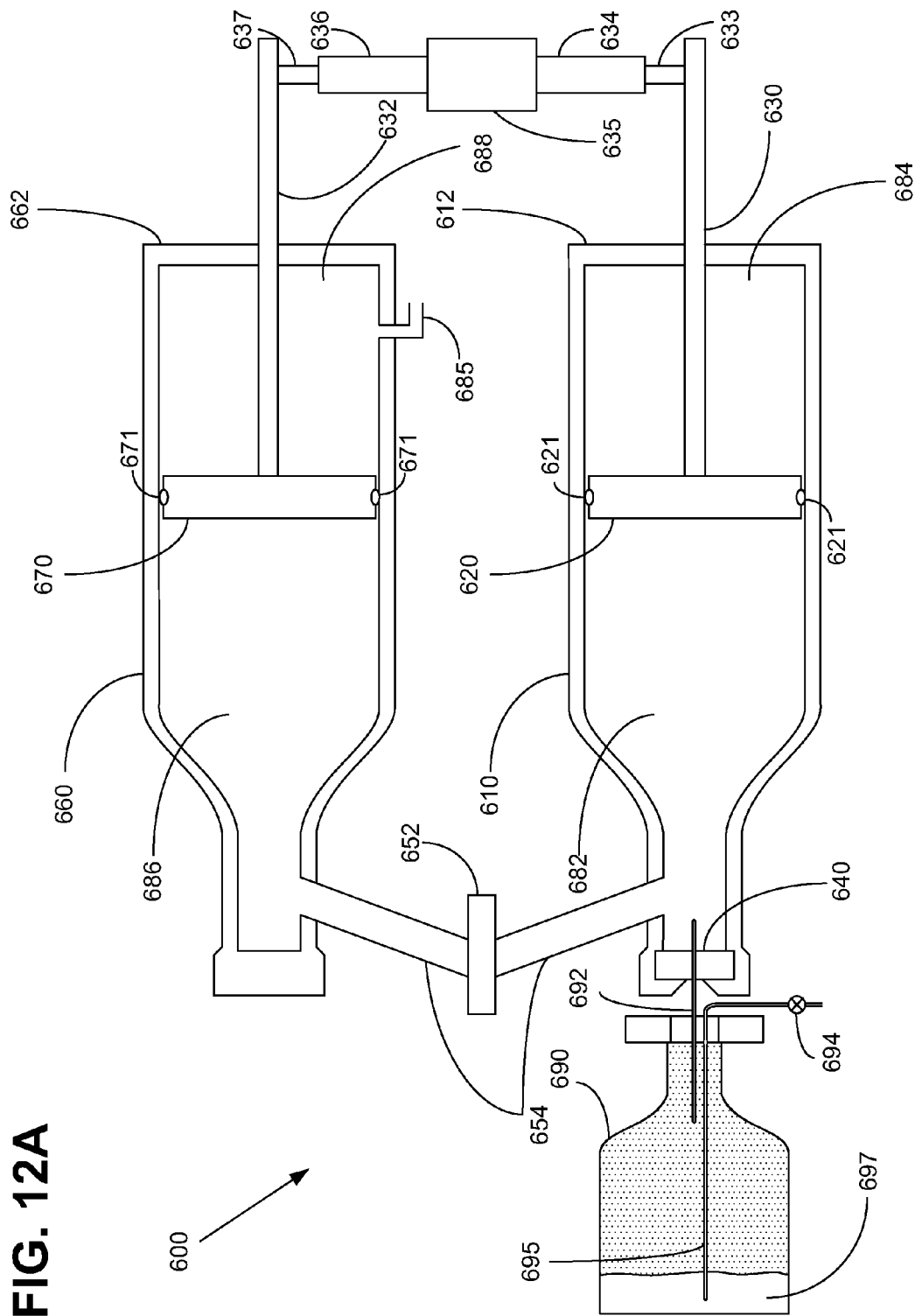
FIG. 12A illustrates a cross-sectional view of a system for managing air bubbles in accordance with an embodiment of the present invention.
Figure 12B:
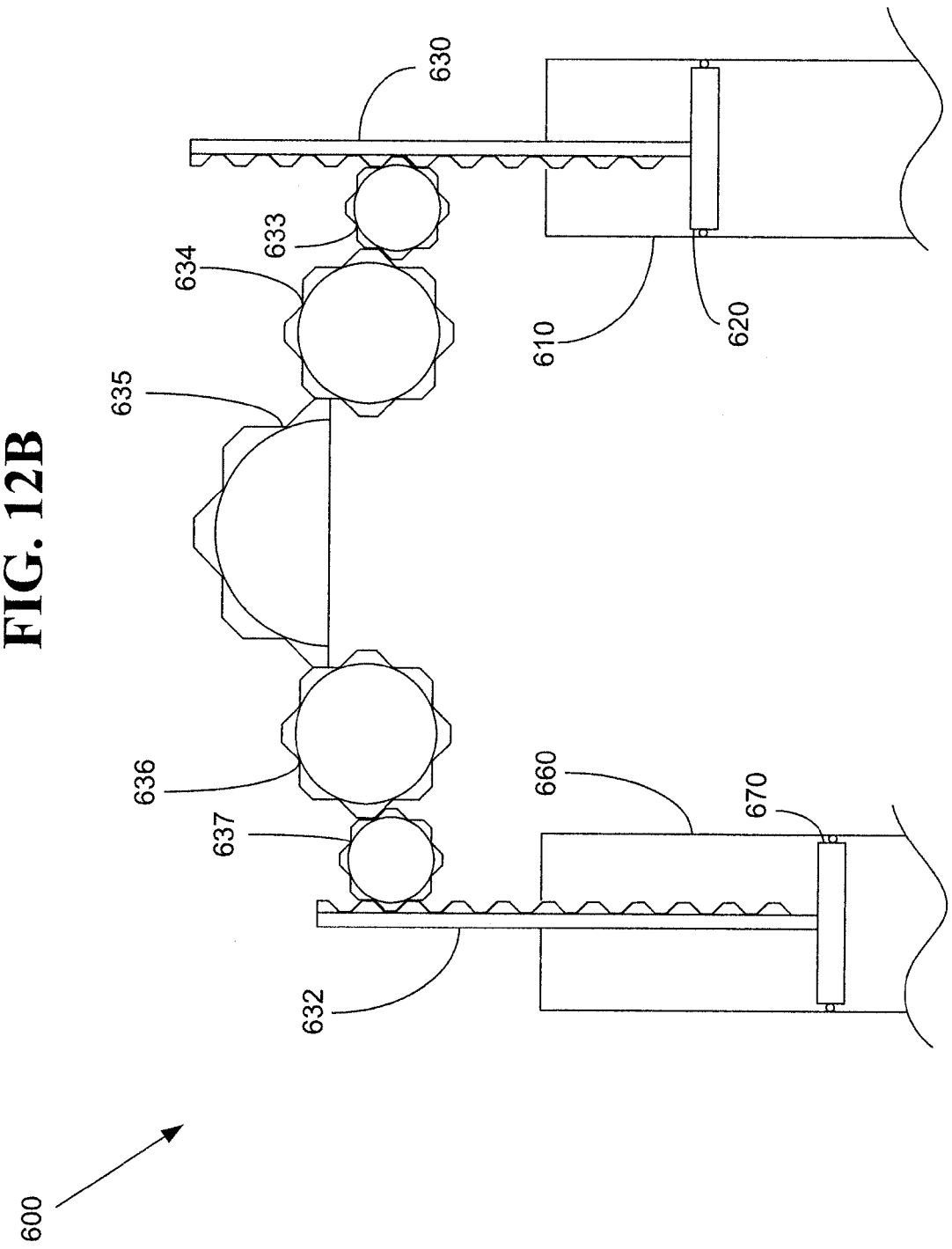
FIG. 12B illustrates a cross-sectional view of a portion of a system for managing air bubbles in accordance with an embodiment of the present invention.

FIGS. 12A and 12B illustrate a cross-sectional view of a system 600 in accordance with an embodiment of the present invention. The system 600 may include, but is not limited to, a first reservoir 610, a first plunger head 620, a second reservoir 660, a second plunger head 670, and a membrane 652. The first plunger head 620 may be positioned within the first reservoir 610. The second plunger head 670 may be positioned within the second reservoir 660.

The first reservoir 610 may have a septum 640. The first reservoir 610 may have an interior volume 682 for containing fluidic media on one side of the first plunger head 620. The first reservoir 610 may have a first chamber 684 on an opposite side of the first plunger head 620 from the interior volume 682 of the first reservoir 610.

The second reservoir 660 may have an interior volume 686 on one side of the second plunger head 670. The interior volume 686 of the second reservoir 660 may be for, but is not limited to, containing air, or the like. The second reservoir 660 may have a second chamber 688 on an opposite side of the second plunger head 670 from the interior volume 686 of the second reservoir 660.

The first plunger head 620 may be moveable in an axial direction within the first reservoir 610 to expand or contract the interior volume 682 of the first reservoir 610. Accordingly, a volume of the first chamber 684 of the first reservoir 610 may contract while the interior volume 682 of the first reservoir 610 expands. The second plunger head 670 may be moveable in an axial direction within the second reservoir 660 to expand or contract the interior volume 686 of the second reservoir 660. Accordingly, a volume of the second chamber 688 of the second reservoir 660 may contract while the interior volume 686 of the second reservoir 660 expands.

The first plunger head 620 may be connected to an end of a first plunger arm 630. The second plunger head 670 may be connected to an end of a second plunger arm 632. The opposite ends of the first plunger arm 630 and the second plunger arm 632 from those connected to the first plunger head 620 and the second plunger head 670, respectively, may be operatively connected to each other.

The first reservoir 610 and the second reservoir 660 may have a passage 654 connecting the interior volume 682 of the first reservoir 610 and the interior volume 686 of the second reservoir 660. The membrane 652 may be positioned in the passage 654. The membrane 652 may be configured such that air may be able to pass from the interior volume 682 of the first reservoir 610 through the passage 654 and the membrane 652 into the interior volume 686 of the second reservoir 660. The membrane 652 may comprise, for example, a hydrophobic material, or the like.

In some embodiments, the first plunger arm 630 and the second plunger arm 632 may be operatively connected to each other with gears for example. In such embodiments, the system 600 may include a handle (not shown). The handle (not shown) may be operatively connected to a half-gear 635, for example. A first intermediate gear 634 may be positioned on one side of the half-gear 635 and may be configured to be operatively engagable to the half-gear 635. A second intermediate gear 636 may be positioned on an other side of the half-gear 635 from the side of the half-gear 635 operatively engagable to the first intermediate gear 634. The second intermediate gear 636 may be configured to be operatively engagable to the half-gear 635.

A first gear 633 may be positioned between the first intermediate gear 634 and the first plunger arm 630 and may be configured to operatively engage each of the first plunger arm 630 and the first intermediate gear 634. A second gear 637 may be positioned between the second intermediate gear 636 and the second plunger arm 632 and may be configured to operatively engage each of the second plunger arm 632 and the second intermediate gear 636. In other embodiments, any suitable configuration of gears may be used to operatively engage each of the first plunger arm 630 and the second plunger arm 632.

The handle (not shown) and the half-gear 635 may be configured such that the half-gear 635 may be rotated as the handle (not shown) is rotated to engage one of the first intermediate gear 634 and the second intermediate gear 636. For example, in a case where the handle (not shown) is rotated counter-clockwise, the half-gear 635 may be rotated counter-clockwise as well to operatively engage the first intermediate gear 634. Once engaged, the half-gear 635 may then rotate the first intermediate gear 634 in a clockwise direction, which may rotate the first gear 633 in a counter-clockwise direction. As the first gear 633 rotates counter-clockwise, the first plunger arm 630 may be moved, for example away from the vial 690. Movement of the first plunger arm 630 and the first plunger head 620 attached to the first plunger arm 630 may cause fluidic media to be drawn from the vial 690 into the interior volume 682 of the first reservoir 610.

As another example, in a case where the handle (not shown) is rotated clockwise, the half-gear 635 may be rotated clockwise as well to operatively engage the second intermediate gear 636. Once engaged, the half-gear 635 may then rotate the second intermediate gear 636 in a counter-clockwise direction, which may rotate the second gear 637 in a clockwise direction. As the second gear 637 rotates clockwise, the second plunger arm 632 may be moved, for example away from the vial 690. Movement of the second plunger arm 632 and the second plunger head 670 attached to the second plunger arm 632 may cause air bubbles in fluidic media contained in the interior volume 682 of the first reservoir 610 to migrate through the passage 654 and the membrane 652 into the interior volume 686 of the second reservoir 660.

The system 600 may include a vial 690 and a needle 692. The vial 690 may be for containing fluidic media. The septum 640 of the first reservoir 610 may be pierceable by the needle 692 to provide a fluid path between the vial 690 and the interior volume 682 of the first reservoir 610. Fluidic media may be drawn from the vial 690 through the needle 692 to the interior volume 682 of the first reservoir 610 in a case where the vial 690 is connected to the first reservoir 610 and the first plunger head 620 is moved within the first reservoir 610 away from the septum 640 of the first reservoir 610. The first plunger head 620 may be moved within the first reservoir 610 to draw fluidic media from the vial 690, for example, by rotating or otherwise operating the handle (not shown).

Similarly, the second plunger head 670 may be moved within the second reservoir 660, for example, by rotating or otherwise operating the handle (not shown). Thus in some embodiments, the first plunger head 620 and the second plunger head 670 may be moved within the first reservoir 610 and the second reservoir 670, respectively, by rotating or otherwise rotating the handle (not shown).

In some embodiments, when the handle (not shown) is rotated or otherwise operated to draw fluidic media from the vial 690 to the interior volume 682 of the first reservoir 610, the membrane 652 and the passage 654 may allow for a transfer of air bubbles from the interior volume 682 of the first reservoir 610 to the interior volume 686 of the second reservoir 660. The membrane 652 may substantially prevent a loss of fluidic media from the interior volume 682 of the first reservoir 610 through the passage 654.

In some embodiments, the system 600 may include a second needle 695. An end of the second needle 695 may be located within a headspace 697 of the vial 690 above fluidic media within the vial 690 in a case where the vial 690 is connected to the first reservoir 610 and the vial is inverted 690. In other embodiments, the end of the second needle 695 may be in contact with fluidic media within the vial 690 in a case where the vial 690 is connected to the first reservoir 610.

An other end of the second needle 695 may be connected to a check valve 694, such as a one-way valve, or the like. The check valve 694 may allow air to enter the vial 690 through the second needle 695. In some embodiments, the check valve 694 may substantially prevent fluidic media from coming out of the vial 690 through the second needle 695 and/or the check valve 694. In various embodiments, the second needle 695 may allow for venting the headspace 697 and/or the vial 690 to atmosphere to facilitate transfer of fluidic media from the vial 690 to the interior volume 682 of the first reservoir 610.

In some embodiments, the second reservoir 660 may have a port 685 for expelling air from the interior volume 686 of the second reservoir 660. Air in the interior volume 686 of the second reservoir 660 may be expelled out the port 685 of the second reservoir 660 in a case where the interior volume 686 of the second reservoir 660 contains air and the interior volume 686 of the second reservoir 660 is in communication with the port 685 of the second reservoir 660. The port 685 of the second reservoir 660 may be in communication with the interior volume 686 of the second reservoir 660 for example, when the second plunger head 670 has been sufficiently moved within the second reservoir 660. An example is illustrated in FIG. 10B, where the second plunger 470 has been sufficiently moved within the second reservoir 460 so that the port 485 of the second reservoir 460 may be in communication with the interior volume 486 of the second reservoir 660.

Figure 13A:
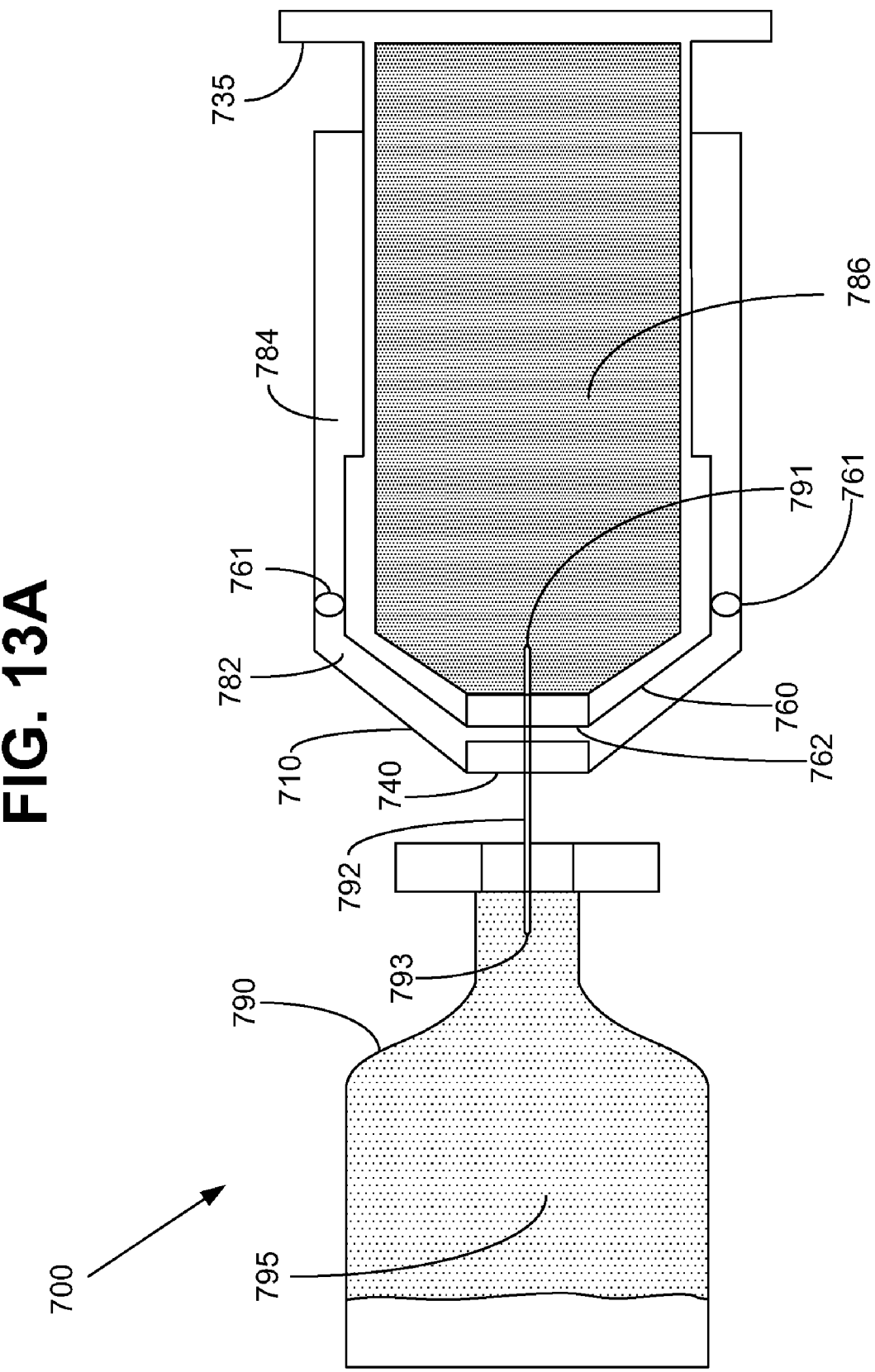
FIG. 13A illustrates a cross-sectional view of a system for transferring fluidic media in accordance with an embodiment of the present invention.
Figure 13C:
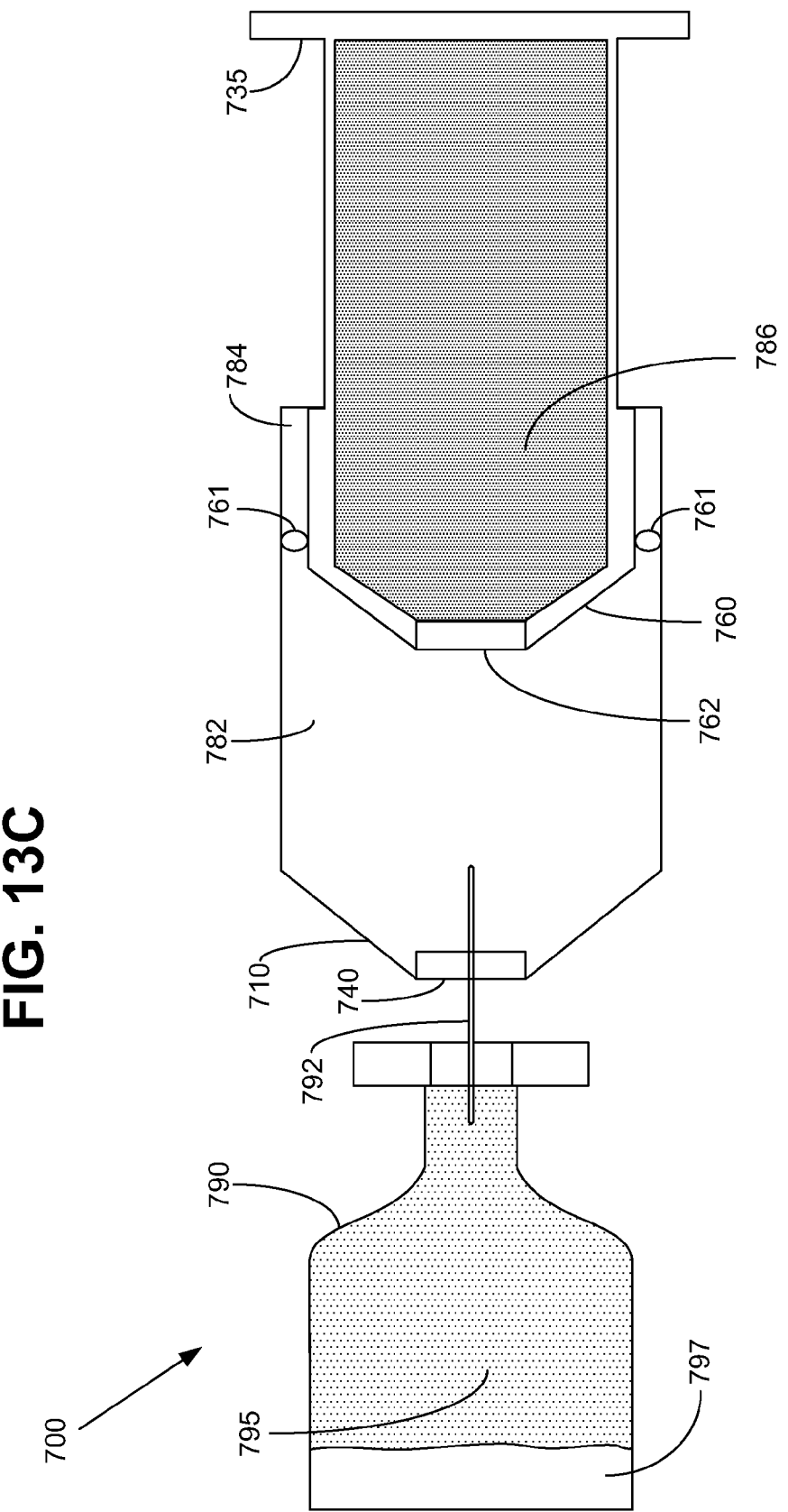
FIG. 13C illustrates a cross-sectional view of a system for transferring fluidic media in accordance with an embodiment of the present invention.

FIGS. 13A-13C illustrate a cross-sectional view of a system 700 in accordance with an embodiment of the present invention. The system 700 may include, but is not limited to, an outer reservoir 710, an inner reservoir 760, and a handle 735. The outer reservoir 710 may include a septum 740. The outer reservoir 710 may have an interior volume 782 for containing fluidic media. The inner reservoir 760 may be configured to be moveable in an axial direction within the outer reservoir 710 to expand or contract the interior volume 782 of the outer reservoir 710. The inner reservoir 760 may include a septum 762. The inner reservoir 760 may have an interior volume 786 for containing a gas, which may be a pressurized gas, such as compressed air, or the like. In some embodiments, the inner reservoir 760 may be a plunger head having an interior volume 786.

The inner reservoir 760 may be connected to a handle 735. The handle 735 may be for moving the inner reservoir 760 within the outer reservoir 710. In other embodiments, the inner reservoir 760 may be connected to an end of a plunger arm (not shown). The plunger arm (not shown) may extend through a back end of the outer reservoir 710 such that an end of the plunger arm (not shown) opposite from the end of the plunger arm (not shown) connected to the inner reservoir 760 may be connected to the handle 735.

A seal member 761, such as an o-ring, may be positioned between the inner reservoir 760 and the outer reservoir 710. The interior volume 782 of the outer reservoir 710 may be on one side of the seal member 761. The outer reservoir 710 may have a chamber 784 located on an opposite side of the seal member 761 from the side of the seal member 761 in contact with the interior volume 782 of the outer reservoir 710. The seal member 761 may be for substantially preventing fluidic media from flowing from the interior volume 782 of the outer reservoir 710 to the chamber 784 of the outer reservoir 710.

The system 700 may include a vial 790 and a needle 792. The vial 790 may be for containing fluidic media. The septum 740 of the outer reservoir 710 may be pierceable by the needle 792 to provide a fluid path between the vial 790 and the interior volume 782 of the outer reservoir 710 in a case where a first end 791 of the needle 792 is in the interior volume 782 of the outer reservoir 710 and a second end 793 of the needle 792 opposite from the first end 791 of the needle 792 is in the vial 790.

The septum 762 of the inner reservoir 760 may be pierceable by the needle 792 to provide a path between the vial 790 and the interior volume 786 of the inner reservoir 760 in a case where the first end 791 of the needle 792 is in the interior volume 786 of the inner reservoir 760 and the second end 793 of the needle 792 is in the vial 790.

In various embodiments, pressure in the interior volume 786 of the inner reservoir 760 may be greater than pressure in the vial 790 prior to the vial 790 being connected to the outer reservoir 710 and the inner reservoir 760. Once connected, pressure in the interior volume 786 of the inner reservoir 760 and in the vial 790 may be substantially equalized relative to one another. Accordingly, pressure in the vial 790 may be greater than pressure in the interior volume 782 of the outer reservoir 710. Thus when the inner reservoir 760 is moved within the outer reservoir 710 to allow the first end 791 of the needle 792 to enter the interior volume 782 of the outer reservoir 710 fluidic media contained in the vial 790 may flow into the interior volume 782 of the outer reservoir 710 in a case where the first end 791 of the needle 792 is in the interior volume 782 of the outer reservoir 710 and pressure in the vial 790 is greater than pressure in the interior volume 782 of the outer reservoir 710.

In operation of the system 700, according to an embodiment of the present invention, the vial 790 may be connected to the outer reservoir 710 and the inner reservoir 760. The needle 792 may pierce the septum 740 of the outer reservoir 710 and the septum 762 of the inner reservoir to establish a path between the vial 790 and the interior volume 786 of the inner reservoir 760. As a result, some of the pressurized gas, such as, compressed air, contained in the interior volume 786 of the inner reservoir 760 may flow into the vial 790 in a case where the first end 791 of the needle 792 is in the interior volume 786 of the inner reservoir 760 and pressure in the interior volume 786 of the inner reservoir 760 is greater than pressure in the vial 790.

The handle 735 may be pulled, for example away from the vial 790, to move the inner reservoir 760 within the outer reservoir 710. The inner reservoir 760 may be moved within the outer reservoir 710 to a point where the first end 791 of the needle 792 is in the interior volume 782 of the outer reservoir 710 as illustrated in FIG. 13B.

Because pressure in the vial 790 has been increased from the compressed air contained in the interior volume 786 of the inner reservoir 760, pressure in the vial 790 may be greater than pressure in the interior volume 782 of the outer reservoir 710. Accordingly, fluidic media in the vial 790 may flow through the needle 792 into the interior volume 782 of the outer reservoir 710 in a case where the first end 791 of the needle 792 is in the interior volume 782 of the outer reservoir 710 and pressure in the vial is greater than pressure in the interior volume 782 of the outer reservoir 710.

In some embodiments, the handle 735 may continue to be pulled to move the inner reservoir 760 within the outer reservoir 710, for example away from the vial 790, such that the interior volume 782 of the outer reservoir 710 may increase and allow fluidic media to be drawn from the vial 790 through the needle 792 into the interior volume 782 of the outer reservoir 710 as illustrated in FIG. 13C. The inner reservoir 760 may be moved within the outer reservoir 710 until the inner reservoir 760 contacts a back end of the outer reservoir 710.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A system for transferring fluidic media, the system comprising:
   an outer reservoir having an interior volume for containing fluidic media; and
   an inner reservoir having an interior volume, the inner reservoir having a septum pierceable by a needle, the needle for providing a path from a vial containing fluidic media to the interior volume of the inner reservoir in a case where a first end of the needle is in the vial and a second end of the needle opposite the first end of the needle is in the interior volume of the inner reservoir;

the outer reservoir having a septum pierceable by the needle, the needle for providing a fluid path from the vial containing fluidic media to the interior volume of the outer reservoir in a case where the first end of the needle is in the vial and the second end of the needle is in the interior volume of the outer reservoir;

at least a portion of the inner reservoir configured to be moveable in the outer reservoir between at least a first inner reservoir position and a second inner reservoir position wherein pressure in the interior volume of the inner reservoir is substantially equal to pressure in the vial when the inner reservoir is in the first inner reservoir position; and wherein pressure in the vial is greater than pressure in the interior volume of the outer reservoir when the inner reservoir is in the second inner reservoir position.

2. The system of claim 1,
wherein the inner reservoir is in the first inner reservoir position when the second end of the needle is in the interior volume of the inner reservoir; and
wherein the inner reservoir is in the second inner reservoir position when the second end of the needle is in the interior volume of the outer reservoir.

3. A method of making a system for transferring fluidic media, the method comprising:
providing an outer reservoir having an interior volume for containing fluidic media;
providing an inner reservoir having an interior volume, the inner reservoir having a septum pierceable by a needle, the needle for providing a path from a vial containing fluidic media to the interior volume of the inner reservoir in a case where a first end of the needle is in the vial and a second end of the needle opposite the first end of the needle is in the interior volume of the inner reservoir;
configuring the outer reservoir to include a septum pierceable by the needle, the needle for providing a fluid path from the vial containing fluidic media to the interior volume of the outer reservoir in a case where the first end of the needle is in the vial and the second end of the needle is in the interior volume of the outer reservoir; and
configuring at least a portion of the inner reservoir to be moveable in the outer reservoir between at least a first inner reservoir position and a second inner reservoir position
wherein pressure in the interior volume of the inner reservoir is substantially equal to pressure in the vial when the inner reservoir is in the first inner reservoir position; and
wherein pressure in the vial is greater than pressure in the interior volume of the outer reservoir when the inner reservoir is in the second inner reservoir position.

4. The system of claim 1, the system further comprising: a seal member positioned between the outer reservoir and the inner reservoir.

5. The system of claim 4, wherein the interior volume of the inner reservoir is on one side of the seal member, and a chamber of the inner reservoir is on an opposite side.

6. The system of claim 1, the system further comprising: a handle arranged to move the inner reservoir within the outer reservoir.

7. A system or transferring fluidic media, the system comprising:

an outer reservoir having an interior volume for containing fluidic media; and an inner reservoir having an interior volume, the inner reservoir having a septum pierceable by a needle, the needle for providing a path from a vial containing fluidic media to the interior volume of the inner reservoir in a case where a first end of the needle is in the vial and a second end of the needle opposite the first end of the needle is in the interior volume of the inner reservoir;

the outer reservoir having a septum pierceable by the needle, the needle for providing a fluid path from the vial containing fluidic media to the interior volume of the outer reservoir in a case where the first end of the needle is in the vial and the second end of the needle is in the interior volume of the outer reservoir;

at least a portion of the inner reservoir configured to be moveable in the outer reservoir between at least a first inner reservoir position and a second inner reservoir position;

wherein the interior volume of the inner reservoir contains pressurized gas.

8. The system of claim 7, wherein the pressurized gas comprises compressed air.

9. The system of claim 7, wherein at least some of the pressurized gas passes through the needle into the vial when the needle pierces the septum of the inner reservoir to increase pressure in the vial.

10. The system of claim 9, wherein a portion of the pressurized gas continues to pass through the needle into the vial when the needle pierces the septum of the inner reservoir until pressure in the interior volume of the inner reservoir is substantially equal to the pressure in the vial.

11. The system of claim 9, wherein the at least some of the pressurized gas forces at least some fluidic media from the vial into the interior volume of the outer reservoir when the second end of the needle is in the interior volume of the outer reservoir.

12. The system of claim 1, wherein pressure in the interior volume of the inner reservoir is greater than pressure in the outer reservoir before the septum of the inner reservoir is pierced by the needle.

13. The system of claim 1, wherein pressure in the interior volume of the inner reservoir is substantially greater than pressure in the vial before the inner reservoir is in the first inner reservoir position.

14. The system of claim 1, the needle for providing the path from the vial to the interior volume of the inner reservoir in a case where the first end of the needle is in contact with fluidic media in the vial and the second end of the needle is in the interior volume of the inner reservoir;
the needle for providing the fluid path from the vial to the interior volume of the outer reservoir in a case where the first end of the needle is in contact with fluidic media in the vial and the second end of the needle is in the interior volume of the outer reservoir.

15. A method of manufacturing a system for transferring fluidic media, the system comprising:
providing an outer reservoir having an interior volume for containing fluidic media;
providing an inner reservoir having an interior volume, the inner reservoir having a septum pierceable by a needle, the needle for providing a path from a vial containing fluidic media to the interior volume of the inner reservoir in a case where a first end of the needle is in the vial and a second end of the needle opposite the first end of the needle is in the interior volume of the inner reservoir;

providing the outer reservoir with a septum pierceable by the needle, the needle for providing a fluid path from the vial containing fluidic media to the interior volume of the outer reservoir in a case where the first end of the needle is in the vial and the second end of the needle is in the interior volume of the outer reservoir; and configuring at least a portion of the inner reservoir to be moveable in the outer reservoir between at least a first inner reservoir position and a second inner reservoir position wherein pressure in the interior volume of the inner reservoir is substantially equal to pressure in the vial when the inner reservoir is in the first inner reservoir position; and wherein pressure in the vial is greater than pressure in the interior volume of the outer reservoir when the inner reservoir is in the second inner reservoir position.

* * * * *